United States Patent
Brown et al.

(10) Patent No.: US 11,255,965 B2
(45) Date of Patent: Feb. 22, 2022

(54) SYSTEMS AND METHODS FOR ULTRASOUND BEAMFORMING USING COHERENTLY COMPOUNDED FRESNEL FOCUSING

(71) Applicant: DALHOUSIE UNIVERSITY, Halifax (CA)

(72) Inventors: Jeremy Brown, Halifax (CA); Christopher Samson, Halifax (CA); Katherine Latham, Dartmouth (CA)

(73) Assignee: DALHOUSIE UNIVERSITY, Halifax (CA)

( * ) Notice: Subject to any disclaimer, the term of this patent is extended or adjusted under 35 U.S.C. 154(b) by 389 days.

(21) Appl. No.: 16/469,903

(22) PCT Filed: Dec. 15, 2017

(86) PCT No.: PCT/CA2017/051524
§ 371 (c)(1),
(2) Date: Jun. 14, 2019

(87) PCT Pub. No.: WO2018/107299
PCT Pub. Date: Jun. 21, 2018

(65) Prior Publication Data
US 2020/0041644 A1 Feb. 6, 2020

Related U.S. Application Data

(60) Provisional application No. 62/434,763, filed on Dec. 15, 2016.

(51) Int. Cl.
*G01S 15/89* (2006.01)
*G01S 7/52* (2006.01)
*A61B 8/08* (2006.01)

(52) U.S. Cl.
CPC ...... *G01S 15/8925* (2013.01); *G01S 15/8927* (2013.01); *G01S 15/8995* (2013.01); *A61B 8/5269* (2013.01); *G01S 7/52095* (2013.01)

(58) Field of Classification Search
CPC ............. G01S 15/8925; G01S 15/8927; G01S 15/8995; G01S 7/52095; G01S 7/52079;
(Continued)

(56) References Cited

U.S. PATENT DOCUMENTS

| 2007/0079658 A1 | 4/2007 | Wagner | |
| 2009/0079299 A1* | 3/2009 | Bradley | G01S 15/8927 310/322 |

(Continued)

FOREIGN PATENT DOCUMENTS

WO 2008033528 A2 3/2008

OTHER PUBLICATIONS

Montaldo et al., "Coherent Plane-Wave Compounding for Very High Frame Rate Ultrasonography and Transient Elastographyl", EEE Trans. Ultra. Ferro. And Freq. Cont. 56, 489 (2009).
(Continued)

*Primary Examiner* — Serkan Akar
*Assistant Examiner* — Renee C Langhals
(74) *Attorney, Agent, or Firm* — Hill & Schumacher

(57) ABSTRACT

Fresnel elevation focusing at a selected elevation angle is performed by transmitting a sequential set of Fresnel-focused ultrasound pulses, where a different Fresnel phase pattern is used for each pulse, and where the receive signals are coherently compounded. The different Fresnel patterns cause the secondary lobe energy to be reduced via averaging of variations of the pressure fields in the secondary lobe regions. In some embodiments, the method of coherently compounded Fresnel focusing is combined with coherently compounded defocused wave (e.g. plane wave or diverging
(Continued)

wave) imaging in the azimuth direction. Each of the elevation slices are collected by changing the Fresnel patterns respectively employed when the sequence of plane waves or diverging waves are transmitted, such that the coherent compounding can benefit both planes simultaneously. Hadamard receive encoding and subsequent dynamic receive beamforming may be employed to further improve performance in the elevation direction.

24 Claims, 23 Drawing Sheets

(58) Field of Classification Search
CPC ............ G01S 15/8959; G01S 15/8993; G01S 7/52047; G01S 7/5202; A61B 8/5269
USPC .......................................................... 600/443
See application file for complete search history.

(56) References Cited

U.S. PATENT DOCUMENTS

2015/0087991 A1* 3/2015 Chen ................... G01S 7/52033
600/459
2015/0289840 A1 10/2015 Konofagou et al.

OTHER PUBLICATIONS

Fong et al., "Comparison of Conventional Parallel Beamforming With Plane Wave and Diverging Wave Imaging for Cardiac Applications: A Simulation Study", IEEE Trans. Ultra. Ferro. And Freq. Cont. 59, 1654 (2012).
Daft et al., "Elevation Beam Profile Control With Bias Polarity Patterns Applied To Microfabricated Ultrasound Transducers", IEEE Ultrasonics Symposium, 1578 (2003).
Papadacci et al., "High-Contrast Ultrafast Imaging of the Heart", IEEE Trans Ultra Ferro. And Freq. Cont. 61, 288 (2014).
Lockwood et al., "Real-Time 3-D Ultrasound Imaging Using Sparse Synthetic Aperture Beamforming", IEEE Trans Ultra. Ferro. And Freq. Cont. 45, 980 (1998).
Tanter et al., "Ultrafast Compound Imaging for 2-D Motion Vector Estimation: Application to Transient Elastography", IEEE Trans. Ultra. Ferro. And Freq. Cont. 49, 1363 (2002).
Latham et al., "Design and preliminary experimental results for a high-frequency crossed electrode phased array, based on a reconfigurable Fresnel lens", IEEE International Ultrasonics symposium Proceedings, Sep. 18-21, 2016, p. 1-4.
Tiran et al., "Multiplane wave imaging increases signal-to-noise ratio in ultrafast ultrasound imaging", Physics in Medicine & biology, IOP Publishing, vol. 60, p. 8549-8566, 2015.
International Search Report PCT/CA2017/051524 dated Mar. 21, 2018.

* cited by examiner

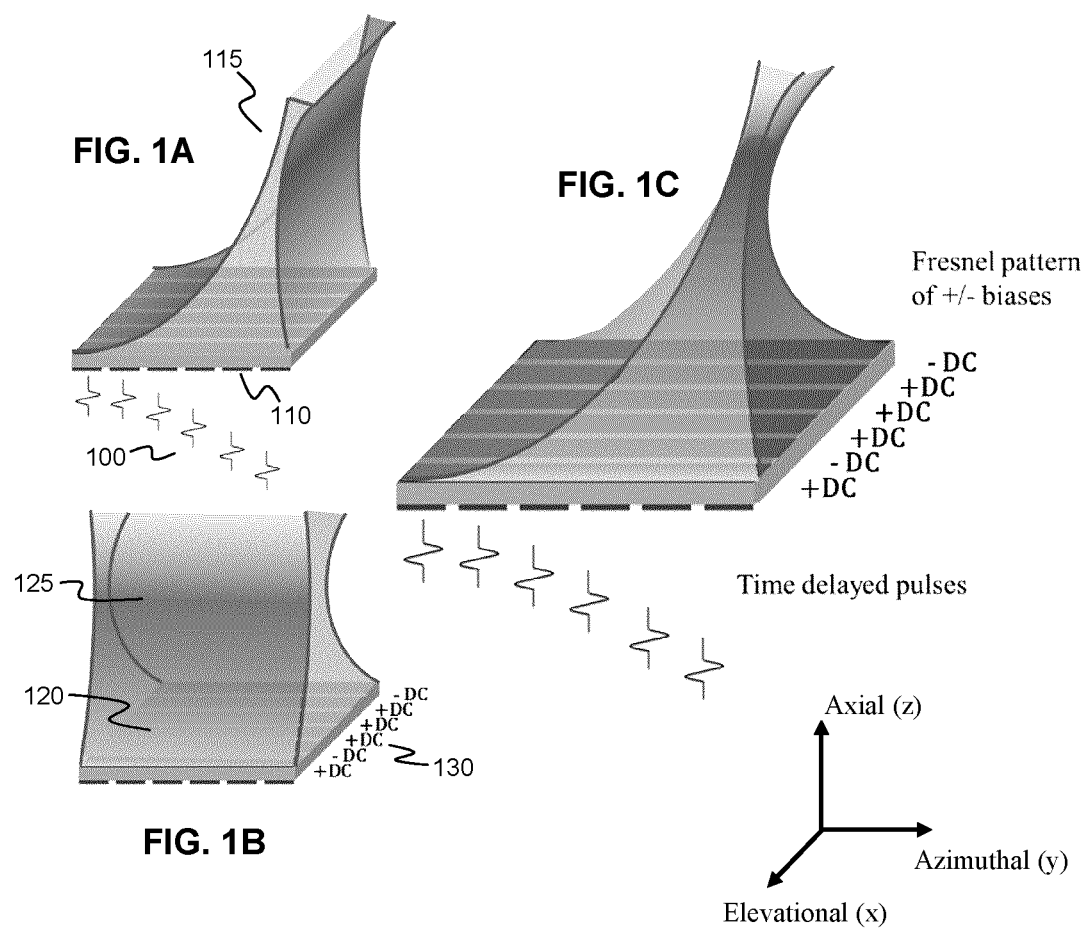

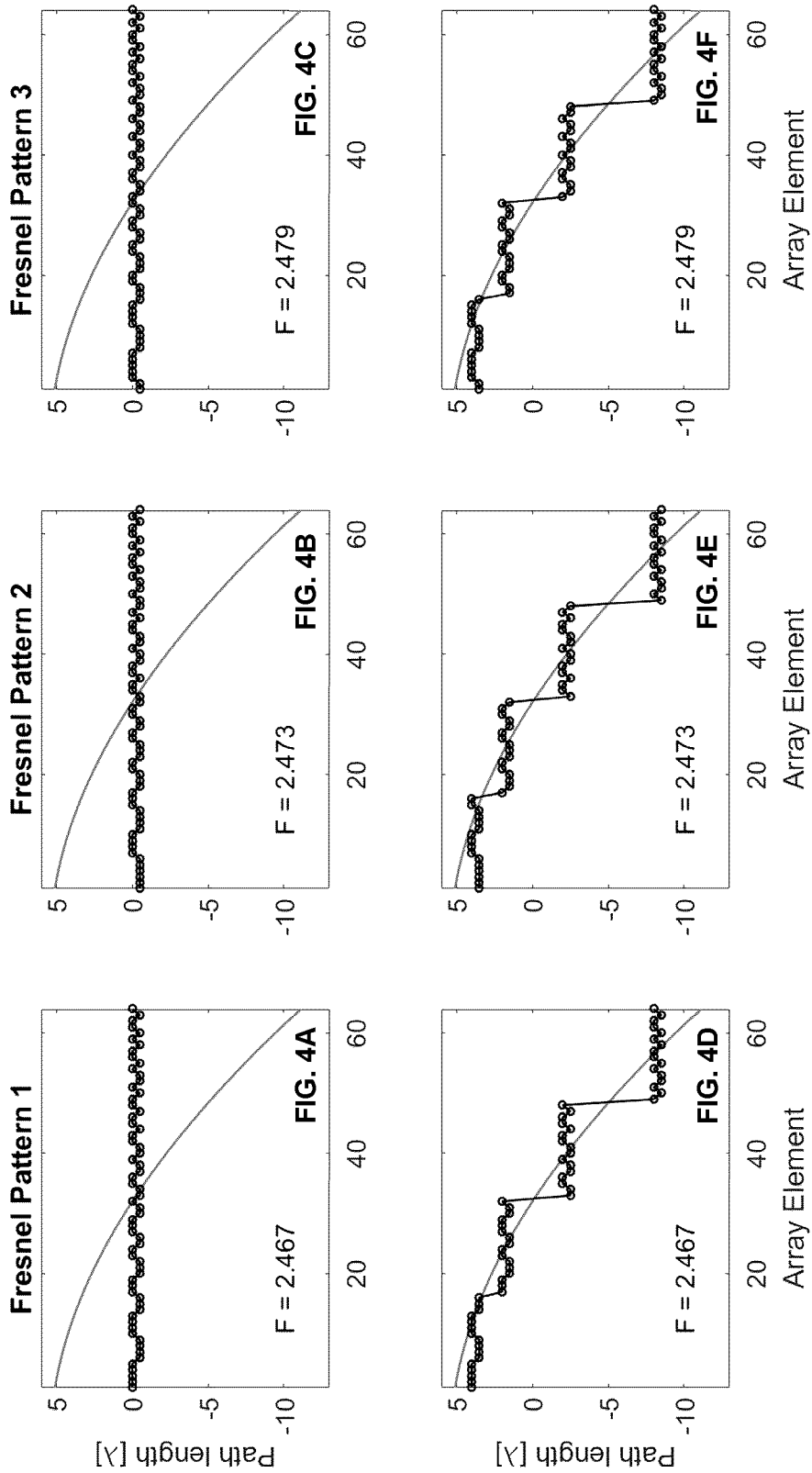

|     | ch1 | ch2 | ch3 | ch4 | ch5 | ch6 | ch7 | ch8 | ch9 | ch10 | ch11 | ch12 | ch13 | ch14 | ch15 | ch16 |
|-----|-----|-----|-----|-----|-----|-----|-----|-----|-----|------|------|------|------|------|------|------|
| H1  | 1 | 1 | 1 | 1 | 1 | 1 | 1 | 1 | 1 | 1 | 1 | 1 | 1 | 1 | 1 | 1 |
| H2  | 1 | -1 | 1 | -1 | 1 | -1 | 1 | -1 | 1 | -1 | 1 | -1 | 1 | -1 | 1 | -1 |
| H3  | 1 | 1 | -1 | -1 | 1 | 1 | -1 | -1 | 1 | 1 | -1 | -1 | 1 | 1 | -1 | -1 |
| H4  | 1 | -1 | -1 | 1 | 1 | -1 | -1 | 1 | 1 | -1 | -1 | 1 | 1 | -1 | -1 | 1 |
| H5  | 1 | 1 | 1 | 1 | -1 | -1 | -1 | -1 | 1 | 1 | 1 | 1 | -1 | -1 | -1 | -1 |
| H6  | 1 | -1 | 1 | -1 | -1 | 1 | -1 | 1 | 1 | -1 | 1 | -1 | -1 | 1 | -1 | 1 |
| H7  | 1 | 1 | -1 | -1 | -1 | -1 | 1 | 1 | 1 | 1 | -1 | -1 | -1 | -1 | 1 | 1 |
| H8  | 1 | -1 | -1 | 1 | -1 | 1 | 1 | -1 | 1 | -1 | -1 | 1 | -1 | 1 | 1 | -1 |
| H9  | 1 | 1 | 1 | 1 | 1 | 1 | 1 | 1 | -1 | -1 | -1 | -1 | -1 | -1 | -1 | -1 |
| H10 | 1 | -1 | 1 | -1 | 1 | -1 | 1 | -1 | -1 | 1 | -1 | 1 | -1 | 1 | -1 | 1 |
| H11 | 1 | 1 | -1 | -1 | 1 | 1 | -1 | -1 | -1 | -1 | 1 | 1 | -1 | -1 | 1 | 1 |
| H12 | 1 | -1 | -1 | 1 | 1 | -1 | -1 | 1 | -1 | 1 | 1 | -1 | -1 | 1 | 1 | -1 |
| H13 | 1 | 1 | 1 | 1 | -1 | -1 | -1 | -1 | -1 | -1 | -1 | -1 | 1 | 1 | 1 | 1 |
| H14 | 1 | -1 | 1 | -1 | -1 | 1 | -1 | 1 | -1 | 1 | -1 | 1 | 1 | -1 | 1 | -1 |
| H15 | 1 | 1 | -1 | -1 | -1 | -1 | 1 | 1 | -1 | -1 | 1 | 1 | 1 | 1 | -1 | -1 |
| H16 | 1 | -1 | -1 | 1 | -1 | 1 | 1 | -1 | -1 | 1 | 1 | -1 | 1 | -1 | -1 | 1 |

FIG. 15

Bias channels

RF channel

Bias channels

RF channels

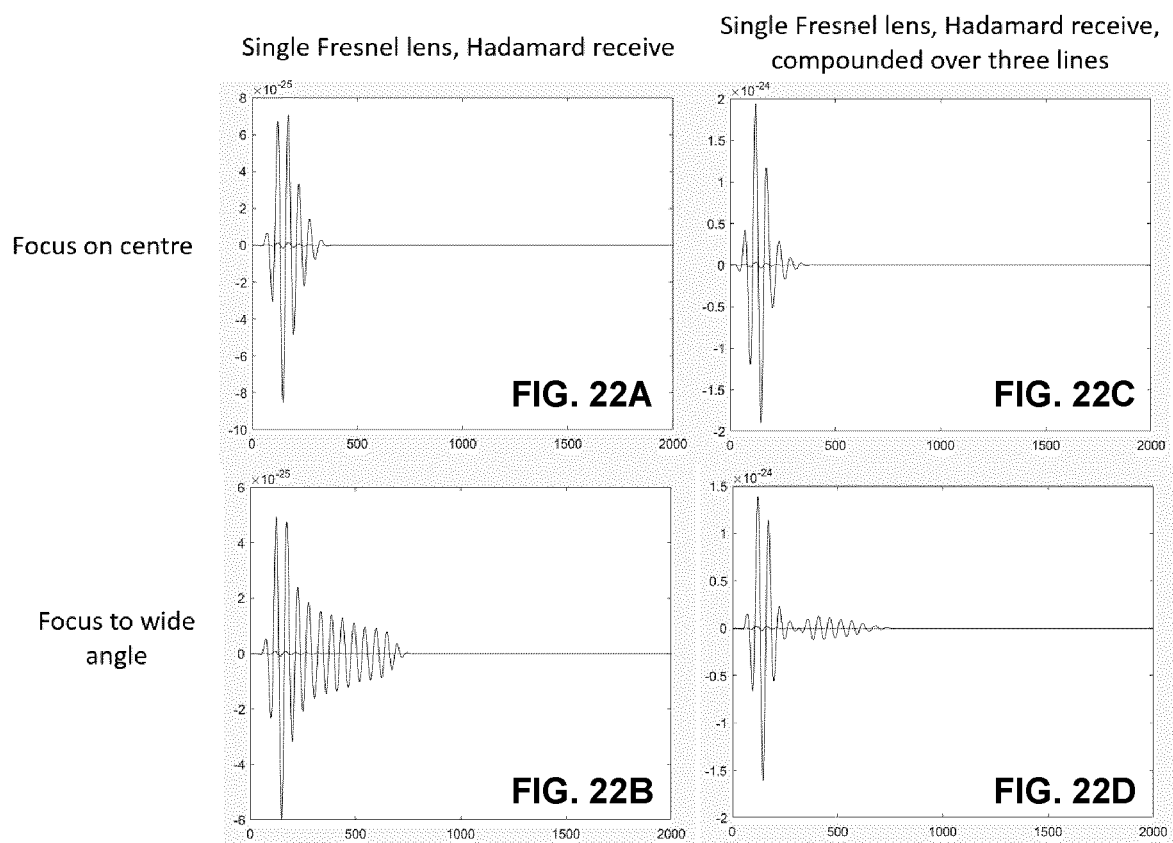

SYSTEMS AND METHODS FOR ULTRASOUND BEAMFORMING USING COHERENTLY COMPOUNDED FRESNEL FOCUSING

CROSS-REFERENCE TO RELATED APPLICATION

This application is a National Phase application claiming the benefit of the international PCT Patent Application No. PCT/CA2017/051524, filed on Dec. 15, 2017, in English, which claims priority to U.S. Provisional Application No. 62/434,763, titled "SYSTEMS AND METHODS FOR ULTRASOUND BEAMFORMING USING COHERENTLY COMPOUNDED FRESNEL FOCUSING" and filed on Dec. 15, 2016, the entire contents of which are incorporated herein by reference.

BACKGROUND

The present disclosure relates to ultrasound beamforming and ultrasound imaging. In some aspects, the present disclosure relates to volumetric ultrasound imaging.

Ultrasound systems capable of 3D imaging present several technical challenges including the number of elements/beamforming channels necessary for a 2D array, electrical matching issues resulting from the high impedance of the small elements and high image acquisition time for a 3D volume. Crossed electrode arrays address some of these issues, especially the huge reduction in number of elements. Instead of a 2D grid of ultrasound elements, a crossed electrode array consists of a linear set of electrodes on the top of the array and an equal but orthogonal set on the bottom of the array. This design maintains electrical control in both planes while reducing the number of elements substantially. However, creating a two-way focused volumetric image in real-time remains difficult with these arrays because azimuth and elevation dimensions cannot be accessed and beamformed at the same time.

Acoustic waves, like light, can be focused using a Fresnel lens or zone plate approach. Fresnel zone plates are capable of producing a tight focus, especially when using a large aperture. A zone plate is made up of rings or strips of alternating transmissive and opaque regions. The waves diffract around the opaque zones and, because of specific spacing of the regions, constructively interfere at the focus. In a Fresnel zone plate, both zones transmit the wave, however, there is a phase reversal in alternating zones. This type of plate has the advantage of greater efficiency and is a good approach for passive ultrasound focusing.

SUMMARY

Fresnel elevation focusing at a selected elevation angle is performed by transmitting a sequential set of Fresnel-focused ultrasound pulses, where a different Fresnel phase pattern is used for each pulse, and where the receive signals are coherently compounded. The different Fresnel patterns cause the secondary lobe energy to be reduced via averaging of variations of the pressure fields in the secondary lobe regions. In some embodiments, the method of coherently compounded Fresnel focusing is combined with coherently compounded defocused wave (e.g. plane wave or diverging wave) imaging in the azimuth direction. Each of the elevation slices are collected by changing the Fresnel patterns respectively employed when the sequence of plane waves or diverging waves are transmitted, such that the coherent compounding can benefit both planes simultaneously. Hadamard receive encoding and subsequent dynamic receive beamforming may be employed to further improve performance in the elevation direction.

Accordingly, in a first aspect, there is provided an ultrasound imaging system comprising:

an ultrasound array comprising a plurality of ultrasound array elements defined between a first electrode array and a second electrode array;

wherein electrodes of said first electrode array are spaced along, and extend perpendicular to, an azimuth direction, and electrodes of said second electrode array are spaced along, and extend perpendicular to, an elevation direction, such that said first electrode array and said second electrode array are provided in a crossed electrode configuration; and wherein each ultrasound array element is capable of acoustic transduction such that a phase of ultrasound waves emitted therefrom is dependent on a polarity of a bias voltage applied thereto;

the ultrasound imaging system further comprising control and processing circuitry operably connected to said first electrode array and said second electrode array, said control and processing circuitry comprising a processor and a memory, wherein said processor is configured to execute instructions stored in said memory for performing the steps of:

a) controlling said ultrasound array to sequentially transmit a plurality of ultrasound pulses such that, for each ultrasound pulse of said plurality of ultrasound pulses, a set of transmit signals are sent to respective electrodes of said first electrode array while providing a set of bias voltages to respective electrodes of said second electrode array;

wherein the transmit signals are provided to said first electrode array such that each ultrasound pulse is unfocused in the azimuth direction, and such that the plurality of ultrasound pulses have respective wavefronts suitable for performing coherent compound imaging in the azimuth direction; and wherein the bias voltages are provided to said second electrode array to form a set of Fresnel phase patterns, wherein each Fresnel phase pattern is configured to focus a respective ultrasound pulse at, or proximal to, a selected elevation slice focus characterized by a selected elevation angle, and wherein at least a subset of the Fresnel phase patterns are different Fresnel phase patterns;

b) coherently compounding receive signals responsively received by said first electrode array after transmitting each ultrasound pulse, thereby obtaining a two-dimensional image data set corresponding to the selected elevation angle, and wherein Fresnel secondary lobes associated with each Fresnel phase pattern are reduced via coherent compounding of the receive signals associated with the different Fresnel phase patterns;

c) repeating steps a) and b) one or more times to collect additional two-dimensional data sets associated with one or more additional elevation angles, thereby obtaining a three-dimensional image data set comprising a plurality of two-dimensional image data sets; and d) processing the three-dimensional image data to generate one or more images.

In another aspect, there is provided a method of controlling an ultrasound array to perform coherent compounded imaging, the ultrasound array comprising a plurality of ultrasound array elements defined between a first electrode array and a second electrode array, wherein electrodes of said first electrode array are spaced along, and extend perpendicular to, an azimuth direction, and wherein electrodes of said second electrode array are spaced along, and extend perpendicular to, an elevation direction, such that said first electrode array and said second electrode array are provided in a crossed electrode configuration, and wherein each ultrasound array element is capable of acoustic transduction such that a phase of ultrasound waves emitted therefrom is dependent on a polarity of a bias voltage applied thereto;

the method comprising:
a) controlling said ultrasound array to sequentially transmit a plurality of ultrasound pulses such that, for each ultrasound pulse of said plurality of ultrasound pulses, a set of transmit signals are sent to respective electrodes of said first electrode array while providing a set of bias voltages to respective electrodes of said second electrode array;
wherein the transmit signals are provided to said first electrode array such that each ultrasound pulse is unfocused in the azimuth direction, and such that the plurality of ultrasound pulses have respective wavefronts suitable for performing coherent compound imaging in the azimuth direction; and
wherein the bias voltages are provided to said second electrode array to form a set of Fresnel phase patterns, wherein each Fresnel phase pattern is configured to focus a respective ultrasound pulse at, or proximal to, a selected elevation slice focus characterized by a selected elevation angle, and wherein at least a subset of the Fresnel phase patterns are different Fresnel phase patterns;
b) coherently compounding receive signals responsively received by said first electrode array after transmitting each ultrasound pulse, thereby obtaining a two-dimensional image data set corresponding to the selected elevation angle, and wherein Fresnel secondary lobes associated with each Fresnel phase pattern are reduced via coherent compounding of the receive signals associated with the different Fresnel phase patterns;
c) repeating steps a) and b) one or more times to collect additional two-dimensional data sets associated with one or more additional elevation angles, thereby obtaining a three-dimensional image data set comprising a plurality of two-dimensional image data sets; and
d) processing the three-dimensional image data to generate one or more images.

In another aspect, there is provided an ultrasound imaging system comprising:
an ultrasound array comprising a plurality of ultrasound array elements defined between a first electrode array and a second electrode array;
wherein electrodes of said first electrode array are spaced along, and extend perpendicular to, an azimuth direction, and electrodes of said second electrode array are spaced along, and extend perpendicular to, an elevation direction, such that said first electrode array and said second electrode array are provided in a crossed electrode configuration; and
wherein each ultrasound array element is capable of acoustic transduction such that a phase of ultrasound waves emitted therefrom is dependent on a polarity of a bias voltage applied thereto;
the ultrasound imaging system further comprising control and processing circuitry operably connected to said first electrode array and said second electrode array, said control and processing circuitry comprising a processor and a memory, wherein said processor is configured to execute instructions stored in said memory for performing the steps of:
a) controlling said ultrasound array to sequentially transmit a plurality of ultrasound pulses such that, for each ultrasound pulse of the plurality of ultrasound pulses, a set of transmit signals are sent to respective electrodes of said first electrode array while providing a set of transmit bias voltages to respective electrodes of said second electrode array;
wherein the transmit signals are provided to said first electrode array such that each ultrasound pulse is unfocused in the azimuth direction, and such that the plurality of ultrasound pulses have respective wavefronts suitable for performing coherent compound imaging in the azimuth direction; and
wherein the transmit bias voltages are provided to said second electrode array to form a Fresnel phase pattern configured to focus a respective ultrasound pulse at a selected elevation slice focus characterized by a selected elevation angle; and
applying receive bias voltages to said second electrode array such that each ultrasound pulse has associated therewith a unique set of receive bias voltages, and wherein the unique sets of receive bias voltages respectively associated with the ultrasound pulses correspond to different rows of a Hadamard matrix;
b) compounding receive signals received by said first electrode array during application of the receive bias voltages for each ultrasound pulse, wherein compounding is performed by:
employing the Hadamard matrix to decode the receive signals, and employing dynamic receive beamforming of the decoded receive signals in the elevation direction to generate a two-way focus associated with the selected elevation angle; and
coherently compounding the decoded and beamformed receive signals to obtain two-dimensional image data set corresponding to the selected elevation angle;
c) repeating steps a) and b) one or more times to collect additional two-dimensional data sets associated with one or more additional elevation angles, thereby obtaining a three-dimensional image data set comprising a plurality of two-dimensional image data sets; and
d) processing the three-dimensional image data to generate one or more images.

In another aspect, there is provided an ultrasound imaging system comprising:
an ultrasound array comprising a plurality of ultrasound array elements defined between a first electrode array and a second electrode array;
wherein electrodes of said first electrode array are spaced along, and extend perpendicular to, an azimuth direction, and electrodes of said second electrode array are spaced along, and extend perpendicular to, an elevation direction, such that said first electrode array and said second electrode array are provided in a crossed electrode configuration; and
wherein each ultrasound array element is capable of acoustic transduction such that a phase of ultrasound waves emitted therefrom is dependent on a polarity of a bias voltage applied thereto;
the ultrasound imaging system further comprising control and processing circuitry operably connected to said first electrode array and said second electrode array, said control and processing circuitry comprising a processor and a memory, wherein said processor is configured to execute instructions stored in said memory for performing the steps of:

a) controlling said ultrasound array to sequentially transmit a plurality of ultrasound pulses such that, for each ultrasound pulse of the plurality of ultrasound pulses, a set of transmit signals are sent to respective electrodes of said first electrode array while providing a set of transmit bias voltages to respective electrodes of said second electrode array;

wherein the transmit signals are provided to said first electrode array such that each ultrasound pulse is unfocused in the azimuth direction, and such that the plurality of ultrasound pulses have respective wavefronts suitable for performing coherent compound imaging in the azimuth direction; and wherein the transmit bias voltages are provided to said second electrode array to form a set of Fresnel phase patterns, wherein each Fresnel phase pattern is configured to form a respective defocused Fresnel wave, and wherein at least a subset of the Fresnel phase patterns are different Fresnel phase patterns, and wherein each Fresnel phase pattern is repeated for a plurality of ultrasound pulses;

applying receive bias voltages to said second electrode array such that each ultrasound pulse corresponding to a given Fresnel phase pattern has associated therewith a unique set of receive bias voltages, and wherein the unique sets of receive bias voltages respectively correspond to different rows of a Hadamard matrix;

b) compounding receive signals received by said first electrode array during application of the receive bias voltages for each ultrasound pulse, wherein compounding is performed by:

employing the Hadamard matrix to decode the receive signals for each Fresnel pattern; and coherently compounding the decoded receive signals in the elevation and azimuthal direction to obtain three dimensional image data; and c) processing the three-dimensional image data to generate one or more images.

In another aspect, there is provided an ultrasound imaging system comprising:

a one-dimensional ultrasound array comprising a plurality of ultrasound array elements defined between a signal electrode array and a bias electrode array, wherein a number of elements of said bias electrode array exceeds a number of electrodes of said signal electrode array, such that said ultrasound array comprises a set of sub-apertures, each sub-aperture comprising a single signal electrode and a plurality of adjacent bias electrodes; and wherein each ultrasound array element is capable of acoustic transduction such that a phase of ultrasound waves emitted therefrom is dependent on a polarity of a bias voltage applied thereto;

the ultrasound imaging system further comprising control and processing circuitry operably connected to said signal electrode array and said bias electrode array, said control and processing circuitry comprising a processor and a memory, wherein said processor is configured to execute instructions stored in said memory for performing the steps of:

a) controlling said ultrasound array to sequentially transmit a plurality of ultrasound pulses such that, for each ultrasound pulse of the plurality of ultrasound pulses, a transmit signal is sent to electrodes of said signal electrode array, and a set of transmit bias voltages are provided to electrodes of said bias electrode array;

wherein the transmit bias voltages are provided to said bias electrode array to form a Fresnel phase pattern configured to focus a respective ultrasound pulse at a selected image line; and applying receive bias voltages to said bias electrode array such that for each sub-aperture, each ultrasound pulse has associated therewith a unique set of receive bias voltages, wherein the unique sets of receive bias voltages respectively associated with the ultrasound pulses correspond to different rows of a Hadamard matrix;

b) compounding receive signals received by each electrode of the signal electrode array during application of the receive bias voltages for each ultrasound pulse, wherein compounding is performed by:

employing the Hadamard matrix to decode the receive signals on a per-sub-aperture basis; and employing dynamic receive beamforming of the decoded receive signals from the sub-apertures to obtain an image line corresponding to the selected image line;

c) repeating steps a) and b) one or more times to collect additional image lines associated with one or more additional image lines, thereby obtaining a two-dimensional image data set; and d) processing the two-dimensional image data to generate one or more images.

In another aspect, there is provided an 45. An ultrasound imaging system comprising:

a one-dimensional ultrasound array comprising a plurality of ultrasound array elements defined between a signal electrode array and a bias electrode array, wherein a number of elements of said bias electrode array exceeds a number of electrodes of said signal electrode array, such that said ultrasound array comprises a set of sub-apertures, each sub-aperture comprising a single signal electrode and a plurality of adjacent bias electrodes; and wherein each ultrasound array element is capable of acoustic transduction such that a phase of ultrasound waves emitted therefrom is dependent on a polarity of a bias voltage applied thereto;

the ultrasound imaging system further comprising control and processing circuitry operably connected to said signal electrode array and said bias electrode array, said control and processing circuitry comprising a processor and a memory, wherein said processor is configured to execute instructions stored in said memory for performing the steps of:

a) controlling said ultrasound array to sequentially transmit a plurality of ultrasound pulses such that, for each ultrasound pulse of the plurality of ultrasound pulses, a transmit signal is sent to electrodes of said signal electrode array, and a set of transmit bias voltages are provided to electrodes of said bias electrode array;

wherein the transmit bias voltages are provided to said bias electrode array to form a set of Fresnel phase patterns, wherein each Fresnel phase pattern is configured to form a respective defocused Fresnel wave, and wherein at least a subset of the Fresnel phase patterns are different Fresnel phase patterns, and wherein each Fresnel phase pattern is repeated for a plurality of ultrasound pulses;

applying receive bias voltages to said bias electrode array such that for each sub-aperture, each ultrasound pulse corresponding to a given Fresnel phase pattern has associated therewith a unique set of receive bias voltages, and wherein the unique sets of receive bias voltages respectively correspond to different rows of a Hadamard matrix;

b) compounding receive signals received by each electrode of the signal electrode array during application of the receive bias voltages for each ultrasound pulse, wherein compounding is performed by:

employing the Hadamard matrix to decode the receive signals on a per-sub-aperture basis for each Fresnel pattern; and coherently compounding the decoded receive signals to obtain two-dimensional image data; and c) processing the two-dimensional image data to generate one or more images.

In another aspect, there is provided an ultrasound imaging system comprising:

a one-dimensional ultrasound array comprising a plurality of ultrasound array elements defined between a signal electrode and a bias electrode array; and wherein each ultrasound array element is capable of acoustic transduction such that a phase of ultrasound waves emitted therefrom is dependent on a polarity of a bias voltage applied thereto;

the ultrasound imaging system further comprising control and processing circuitry operably connected to said signal electrode and said bias electrode array, said control and processing circuitry comprising a processor and a memory, wherein said processor is configured to execute instructions stored in said memory for performing the steps of:

a) controlling said ultrasound array to sequentially transmit a plurality of ultrasound pulses such that, for each ultrasound pulse of the plurality of ultrasound pulses, a transmit signal is sent to said signal electrode, and a set of transmit bias voltages are provided to electrodes of said bias electrode array;

wherein the transmit bias voltages are provided to said bias electrode array to form a Fresnel phase pattern configured to focus a respective ultrasound pulse at a selected image line; and applying receive bias voltages to said bias electrode array such that each ultrasound pulse has associated therewith a unique set of receive bias voltages, wherein the unique sets of receive bias voltages respectively associated with the ultrasound pulses correspond to different rows of a Hadamard matrix;

b) compounding receive signals received by the signal electrode during application of the receive bias voltages for each ultrasound pulse, wherein compounding is performed by:

employing the Hadamard matrix to decode the receive signals on a per-sub-aperture basis; and employing dynamic receive beamforming of the decoded receive signals to obtain an image line corresponding to the selected image line;

c) repeating steps a) and b) one or more times to collect additional image lines associated with one or more additional image lines, thereby obtaining a two-dimensional image data set; and d) processing the two-dimensional image data to generate one or more images.

In another aspect, there is provided an ultrasound imaging system comprising:

a one-dimensional ultrasound array comprising a plurality of ultrasound array elements defined between a signal electrode and a bias electrode array; and wherein each ultrasound array element is capable of acoustic transduction such that a phase of ultrasound waves emitted therefrom is dependent on a polarity of a bias voltage applied thereto;

the ultrasound imaging system further comprising control and processing circuitry operably connected to said signal electrode and said bias electrode array, said control and processing circuitry comprising a processor and a memory, wherein said processor is configured to execute instructions stored in said memory for performing the steps of:

a) controlling said ultrasound array to sequentially transmit a plurality of ultrasound pulses such that, for each ultrasound pulse of the plurality of ultrasound pulses, a transmit signal is sent to said signal electrode, and a set of transmit bias voltages are provided to electrodes of said bias electrode array;

wherein the transmit bias voltages are provided to said bias electrode array to form a set of Fresnel phase patterns, wherein each Fresnel phase pattern is configured to form a respective defocused Fresnel wave, and wherein at least a subset of the Fresnel phase patterns are different Fresnel phase patterns, and wherein each Fresnel phase pattern is repeated for a plurality of ultrasound pulses;

applying receive bias voltages to said bias electrode array such that each ultrasound pulse corresponding to a given Fresnel phase pattern has associated therewith a unique set of receive bias voltages, and wherein the unique sets of receive bias voltages respectively correspond to different rows of a Hadamard matrix;

b) compounding receive signals received by the signal electrode during application of the receive bias voltages for each ultrasound pulse, wherein compounding is performed by:

employing the Hadamard matrix to decode the receive signals for each Fresnel pattern; and coherently compounding the decoded receive signals to obtain two-dimensional image data; and c) processing the two-dimensional image data to generate one or more images.

In another aspect, there is provided a method of performing imaging with an ultrasound array, said ultrasound array comprising a plurality of ultrasound array elements defined between a first electrode array and a second electrode array, wherein electrodes of said first electrode array are spaced along, and extend perpendicular to, an azimuth direction, and electrodes of said second electrode array are spaced along, and extend perpendicular to, an elevation direction, such that said first electrode array and said second electrode array are provided in a crossed electrode configuration; and wherein each ultrasound array element is capable of acoustic transduction such that a phase of ultrasound waves emitted therefrom is dependent on a polarity of a bias voltage applied thereto;

the method comprising:

a) controlling said ultrasound array to sequentially transmit a plurality of ultrasound pulses such that, for each ultrasound pulse of the plurality of ultrasound pulses, a set of transmit signals are sent to respective electrodes of said first electrode array while providing a set of transmit bias voltages to respective electrodes of said second electrode array;

wherein the transmit signals are provided to said first electrode array such that each ultrasound pulse is unfocused in the azimuth direction, and such that the plurality of ultrasound pulses have respective wavefronts suitable for performing coherent compound imaging in the azimuth direction; and wherein the transmit bias voltages are provided to said second electrode array to form a Fresnel phase pattern configured to focus a respective ultrasound pulse at a selected elevation slice focus characterized by a selected elevation angle; and applying receive bias voltages to said second electrode array such that each ultrasound pulse has associated therewith a unique set of receive bias voltages, and wherein the unique sets of receive bias voltages respectively associated with the ultrasound pulses correspond to different rows of a Hadamard matrix;

b) compounding receive signals received by said first electrode array during application of the receive bias voltages for each ultrasound pulse, wherein compounding is performed by:

employing the Hadamard matrix to decode the receive signals, and employing dynamic receive beamforming of the decoded receive signals in the elevation direction to generate a two-way focus associated with the selected elevation angle; and coherently compounding the decoded and beamformed receive signals to obtain two-dimensional image data set corresponding to the selected elevation angle;

c) repeating steps a) and b) one or more times to collect additional two-dimensional data sets associated with one or more additional elevation angles, thereby obtaining a three-dimensional image data set comprising a plurality of two-dimensional image data sets; and d) processing the three-dimensional image data to generate one or more images.

In another aspect, there is provided a 53. A method of performing imaging with an ultrasound array, said ultrasound array comprising a plurality of ultrasound array elements defined between a first electrode array and a second electrode array; wherein electrodes of said first electrode array are spaced along, and extend perpendicular to, an azimuth direction, and electrodes of said second electrode array are spaced along, and extend perpendicular to, an elevation direction, such that said first electrode array and said second electrode array are provided in a crossed electrode configuration; and wherein each ultrasound array element is capable of acoustic transduction such that a phase of ultrasound waves emitted therefrom is dependent on a polarity of a bias voltage applied thereto;

the method comprising:

a) controlling said ultrasound array to sequentially transmit a plurality of ultrasound pulses such that, for each ultrasound pulse of the plurality of ultrasound pulses, a set of transmit signals are sent to respective electrodes of said first electrode array while providing a set of transmit bias voltages to respective electrodes of said second electrode array;

wherein the transmit signals are provided to said first electrode array such that each ultrasound pulse is unfocused in the azimuth direction, and such that the plurality of ultrasound pulses have respective wavefronts suitable for performing coherent compound imaging in the azimuth direction; and wherein the transmit bias voltages are provided to said second electrode array to form a set of Fresnel phase patterns, wherein each Fresnel phase pattern is configured to form a respective defocused Fresnel wave, and wherein at least a subset of the Fresnel phase patterns are different Fresnel phase patterns, and wherein each Fresnel phase pattern is repeated for a plurality of ultrasound pulses;

applying receive bias voltages to said second electrode array such that each ultrasound pulse corresponding to a given Fresnel phase pattern has associated therewith a unique set of receive bias voltages, and wherein the unique sets of receive bias voltages respectively correspond to different rows of a Hadamard matrix;

b) compounding receive signals received by said first electrode array during application of the receive bias voltages for each ultrasound pulse, wherein compounding is performed by:

employing the Hadamard matrix to decode the receive signals for each Fresnel pattern; and coherently compounding the decoded receive signals in the elevation and azimuthal direction to obtain three dimensional image data; and c) processing the three-dimensional image data to generate one or more images.

In another aspect, there is provided a method of performing imaging with a one-dimensional ultrasound array, the one-dimensional ultrasound array comprising a plurality of ultrasound array elements defined between a signal electrode array and a bias electrode array, wherein a number of elements of said bias electrode array exceeds a number of electrodes of said signal electrode array, such that said ultrasound array comprises a set of sub-apertures, each sub-aperture comprising a single signal electrode and a plurality of adjacent bias electrodes; and wherein each ultrasound array element is capable of acoustic transduction such that a phase of ultrasound waves emitted therefrom is dependent on a polarity of a bias voltage applied thereto;

the ultrasound imaging system further comprising control and processing circuitry operably connected to said signal electrode array and said bias electrode array, said control and processing circuitry comprising a processor and a memory, wherein said processor is configured to execute instructions stored in said memory for performing the steps of:

a) controlling said ultrasound array to sequentially transmit a plurality of ultrasound pulses such that, for each ultrasound pulse of the plurality of ultrasound pulses, a transmit signal is sent to electrodes of said signal electrode array, and a set of transmit bias voltages are provided to electrodes of said bias electrode array;

wherein the transmit bias voltages are provided to said bias electrode array to form a Fresnel phase pattern configured to focus a respective ultrasound pulse at a selected image line; and applying receive bias voltages to said bias electrode array such that for each sub-aperture, each ultrasound pulse has associated therewith a unique set of receive bias voltages, wherein the unique sets of receive bias voltages respectively associated with the ultrasound pulses correspond to different rows of a Hadamard matrix;

b) compounding receive signals received by each electrode of the signal electrode array during application of the receive bias voltages for each ultrasound pulse, wherein compounding is performed by:

employing the Hadamard matrix to decode the receive signals on a per-sub-aperture basis; and employing dynamic receive beamforming of the decoded receive signals from the sub-apertures to obtain an image line corresponding to the selected image line;

c) repeating steps a) and b) one or more times to collect additional image lines associated with one or more additional image lines, thereby obtaining a two-dimensional image data set; and d) processing the two-dimensional image data to generate one or more images.

In another aspect, there is provided a method of performing imaging with a one-dimensional ultrasound array, the one-dimensional ultrasound array comprising a plurality of ultrasound array elements defined between a signal electrode array and a bias electrode array, wherein a number of elements of said bias electrode array exceeds a number of electrodes of said signal electrode array, such that said ultrasound array comprises a set of sub-apertures, each sub-aperture comprising a single signal electrode and a plurality of adjacent bias electrodes; and wherein each ultrasound array element is capable of acoustic transduction such that a phase of ultrasound waves emitted therefrom is dependent on a polarity of a bias voltage applied thereto; the method comprising:

a) controlling said ultrasound array to sequentially transmit a plurality of ultrasound pulses such that, for each ultrasound pulse of the plurality of ultrasound pulses, a transmit signal is sent to electrodes of said signal electrode array, and a set of transmit bias voltages are provided to electrodes of said bias electrode array;

wherein the transmit bias voltages are provided to said bias electrode array to form a set of Fresnel phase patterns, wherein each Fresnel phase pattern is configured to form a respective defocused Fresnel wave, and wherein at least a subset of the Fresnel phase patterns are different Fresnel phase patterns, and wherein each Fresnel phase pattern is repeated for a plurality of ultrasound pulses;

applying receive bias voltages to said bias electrode array such that for each sub-aperture, each ultrasound pulse corresponding to a given Fresnel phase pattern has associated therewith a unique set of receive bias voltages, and wherein the unique sets of receive bias voltages respectively correspond to different rows of a Hadamard matrix;

b) compounding receive signals received by each electrode of the signal electrode array during application of the receive bias voltages for each ultrasound pulse, wherein compounding is performed by:
  employing the Hadamard matrix to decode the receive signals on a per-sub-aperture basis for each Fresnel pattern; and
  coherently compounding the decoded receive signals to obtain two-dimensional image data; and c) processing the two-dimensional image data to generate one or more images.

In another aspect, there is provided a method of performing imaging with a one-dimensional ultrasound array, the one-dimensional ultrasound array comprising a plurality of ultrasound array elements defined between a signal electrode and a bias electrode array; wherein each ultrasound array element is capable of acoustic transduction such that a phase of ultrasound waves emitted therefrom is dependent on a polarity of a bias voltage applied thereto; the method comprising:

a) controlling said ultrasound array to sequentially transmit a plurality of ultrasound pulses such that, for each ultrasound pulse of the plurality of ultrasound pulses, a transmit signal is sent to said signal electrode, and a set of transmit bias voltages are provided to electrodes of said bias electrode array;

wherein the transmit bias voltages are provided to said bias electrode array to form a Fresnel phase pattern configured to focus a respective ultrasound pulse at a selected image line; and applying receive bias voltages to said bias electrode array such that each ultrasound pulse has associated therewith a unique set of receive bias voltages, wherein the unique sets of receive bias voltages respectively associated with the ultrasound pulses correspond to different rows of a Hadamard matrix;

b) compounding receive signals received by the signal electrode during application of the receive bias voltages for each ultrasound pulse, wherein compounding is performed by:
  employing the Hadamard matrix to decode the receive signals on a per-sub-aperture basis; and
  employing dynamic receive beamforming of the decoded receive signals to obtain an image line corresponding to the selected image line;

c) repeating steps a) and b) one or more times to collect additional image lines associated with one or more additional image lines, thereby obtaining a two-dimensional image data set; and d) processing the two-dimensional image data to generate one or more images.

In another aspect, there is provided a method of performing imaging with a one-dimensional ultrasound array, the one-dimensional ultrasound array comprising a plurality of ultrasound array elements defined between a signal electrode and a bias electrode array; wherein each ultrasound array element is capable of acoustic transduction such that a phase of ultrasound waves emitted therefrom is dependent on a polarity of a bias voltage applied thereto;

the method comprising:

a) controlling said ultrasound array to sequentially transmit a plurality of ultrasound pulses such that, for each ultrasound pulse of the plurality of ultrasound pulses, a transmit signal is sent to said signal electrode, and a set of transmit bias voltages are provided to electrodes of said bias electrode array;

wherein the transmit bias voltages are provided to said bias electrode array to form a set of Fresnel phase patterns, wherein each Fresnel phase pattern is configured to form a respective defocused Fresnel wave, and wherein at least a subset of the Fresnel phase patterns are different Fresnel phase patterns, and wherein each Fresnel phase pattern is repeated for a plurality of ultrasound pulses;

applying receive bias voltages to said bias electrode array such that each ultrasound pulse corresponding to a given Fresnel phase pattern has associated therewith a unique set of receive bias voltages, and wherein the unique sets of receive bias voltages respectively correspond to different rows of a Hadamard matrix;

b) compounding receive signals received by the signal electrode during application of the receive bias voltages for each ultrasound pulse, wherein compounding is performed by:
  employing the Hadamard matrix to decode the receive signals for each Fresnel pattern; and
  coherently compounding the decoded receive signals to obtain two-dimensional image data; and c) processing the two-dimensional image data to generate one or more images.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 1A-C illustrate various focusing configurations using a crossed electrode array, showing (A) the focus created by traditional beamforming in the azimuth direction, (B) the focus created in the elevation direction by steerable Fresnel lens and (C) the combination of the two focusing types.

FIGS. 4A-C show an example Fresnel phase pattern for three different transmit/receive events generated by changing the location of the focus for a 15 degree steering angle.

FIGS. 4D-F show example Fresnel patterns for three different transmit/receive events generated by changing the location of the focus for a 15 degree steering angle, where a split and delay sub-aperture technique is combined with the unique Fresnel phase patterns, such that a set of sub-apertures are employed for each transmit/receive event.

FIGS. 9A, 9C and 9E plot the individual receive signals corresponding to each transmit/receive event, and FIGS. 9B, 9D and 9F show the coherently compounded receive signals.

FIGS. 12A, 12C and 12E plot the individual receive signals corresponding to each transmit/receive event, and FIGS. 12B, 12D and 12F show the coherently compounded receive signals.

FIG. 15 is an example of a Hadamard matrix, showing an example 16×16 matrix.

FIGS. 22A-22D are plots that demonstrate the effect of compounding neighbouring image lines on pulse length for a one-dimensional array, showing (A) the processed pulse for a single Fresnel lens on transmit and Hadamard receive encoding, with a focus on center, (B) the processed pulse for a single Fresnel lens on transmit and Hadamard receive encoding, with a focus to a wide angle, (C) the processed pulse for a single Fresnel lens on transmit and Hadamard receive encoding and compounding of three neighbouring lines, with a focus on center, and (B) the processed pulse for a single Fresnel lens on transmit and Hadamard receive encoding and compounding of three neighbouring lines, with a focus to a wide angle. The vertical axis is arbitrary pulse amplitude, and the horizontal axis is time.

DETAILED DESCRIPTION

Figure 2A:
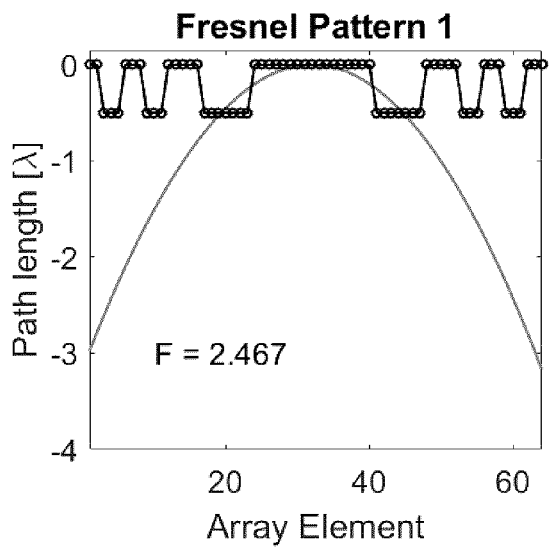
FIGS. 2A-C illustrate Fresnel patterns for three different sequential transmit/receive events, where the different Fresnel patterns correspond to foci having different on-axis locations.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Fresnel Zone Plates in Ultrasound Beamforming and Imaging

Implementing a Fresnel approach in an ultrasound transducer requires control of the pulse polarity. Arrays built on either electrostrictive ceramics or CMUTs are appropriate for this approach because the phase is controlled by the polarity of a DC bias and can be changed dynamically. Electrostrictive ceramics such as PMN-PT (lead magnesium niobate-lead titanate) ceramic can be used as the array substrate in place of conventional piezoelectrics. This type of material is only piezoelectrically active while a bias voltage is applied. In addition, the response is tunable with the amplitude of the bias voltage. When no voltage applied to the transducer, the response is negligible, and when a DC bias is applied, the phase of the acoustic wave produced is quantized to either +90 or −90 degrees, depending on whether the bias is positive or negative. Array elements defined on an electrostrictive substrate can therefore be addressed individually and in parallel. This allows for reconfigurable Fresnel zone plates to be created by varying biasing patterns with positive and negative values across the array.

Typical linear-phased arrays use an acoustic lens to improve the elevational slice resolution (slice thickness) of the image. If an elevation lens could be reconfigured to steer to moderate angles, then a volumetric image could be captured without adding additional beamforming channels and only moderately increasing the number of electrical connections. This can be accomplished by replacing the mechanical acoustic lens with an electrically reconfigurable lens that approximates a Fresnel lens.

As described above, a Fresnel lens is created by applying the appropriate pattern of positive and negative biases along the elevation direction of the array which determine the polarity of the pulses from each element. Concurrently, beamforming can be performed in the other plane using the orthogonal electrodes. In one example implementation, the array is formed having a set of bottom electrodes running orthogonal to the top electrodes, similar to a crossed electrode array. The bottom electrodes provide the active lens control in the elevation plane (or vice versa).

FIGS. 1A-C illustrate the steerable lens concept on a crossed electrode array in which a dynamic Fresnel lens is employed for elevation focusing. FIG. 1A shows the use of conventional transmit phased array beamforming in the azimuth direction. A set of transmit signals 100 are sent to the bottom electrode array 110, and a beamformed pulse 115 is transmitted and focused in the azimuth direction.

FIG. 1B shows the use of Fresnel focusing in the elevation direction, in which a Fresnel phase plate (lens) is formed via control of the bias voltages 130 applied to the second array 120. The set of bias voltages 130 are provided to the second array such that the ultrasound waves emitted by the transducer elements in the elevation direction differ in phase by 0 or 180°, thereby forming a discrete Fresnel phase profile that focuses the transmitted waves in the elevation direction. This phase profile across the ultrasound elements is henceforth referred to as a Fresnel phase pattern.

When creating a Fresnel type focus in the elevation direction, the bias value for each element is calculated by considering the geometric path length between the element and the focus. The relative phase delay for that element is given as:

$$\varphi = 2\pi[z - \sqrt{x^2 + z^2}]/\lambda, \quad (1)$$

where x and z are the coordinates, in the elevation and axial directions, respectively (see FIGS. 1A-C), of the desired focus relative to the array element and λ is the wavelength of the centre frequency of the excitation pulse in the medium. The sign of the bias ($S_{bias}$) is given as follows:

$$S_{bias} = \text{sign}[\text{mod}(\varphi + \text{offset}, -2\pi) + \pi] \quad (2)$$

This is a phase wrapped approximation of the relative phase delay for each element. The portion of the delay that falls within a single wavelength is then quantized as 0 or π radians (effective delays are equivalent to 0 or λ/2). This models the purely transparent regions and the pulse inverted regions of the Fresnel zone plate. An offset phase can be added in the calculation that shifts the reference phase of the center element. Therefore, there is not one unique Fresnel pattern for a given focal point. The pattern can be chosen to optimize for different beam shapes (e.g. main lobe width, secondary lobe level, sensitivity). The Fresnel approach is an approximation compared to conventional beamforming and could be thought of as having beamformer delay resolution quantized to only half a wavelength.

FIG. 1C illustrates a hybrid case, in which conventional beamforming is employed for focusing in the azimuth direction, while Fresnel beamforming is employed for focusing in the elevation direction. Unfortunately, the two-way beam profile using a Fresnel focus in the elevation direction results in high secondary lobe energy, preventing this technique from producing useful diagnostic images.

Compounded Fresnel Imaging

Example embodiments of the present disclosure address the aforementioned problem of high secondary lobe energy that is associated with Fresnel focusing and imaging. According to various example embodiments described below, Fresnel focusing at a selected elevation angle is performed by transmitting a sequential set of Fresnel-focused ultrasound pulses, where different Fresnel phase patterns are employed when transmitting the ultrasound pulses. In contrast to known methods of synthetic aperture Fresnel focusing in which a plurality of ultrasound pulses are sequentially transmitted from different Fresnel sub-apertures based on a single Fresnel phase pattern for the full Fresnel aperture, various example embodiments described below employ the sequential transmission of ultrasound pulses from the full Fresnel aperture, where different Fresnel phase patterns are employed when transmitting each Fresnel-focused ultrasound pulses. The signals that are sequentially received in response to the different transmit events are coherently combined, and the method is henceforth referred to as coherently compounded Fresnel focusing or coherently compounded Fresnel imaging.

The inventors have found that when such a coherently compounded Fresnel focusing scheme is employed, where different Fresnel phase patterns are employed to focus the different ultrasound pulses, the coherent combining of the received signals causes the secondary lobe energy to be reduced via the averaging of variations of the pressure fields in the secondary lobe regions. In other words, the averaging of the pressure fields in the secondary lobe regions, each with random beamforming delay errors quantized to $\lambda/2$, results in the reduction of the secondary lobe energy. Without intending to be limited by theory, it is believed that a reduction in secondary lobe energy of up to $1/\sqrt{n}$ may be achieved relative to imaging with a single Fresnel aperture having a single Fresnel phase pattern, where n is the number of transmitted pulses having different associated Fresnel phase patterns.

The coherently compounded Fresnel approach disclosed herein is advantageously capable of enabling dynamic steering and collection of elevation slices, in contrast to a fixed mechanical lens.

The different Fresnel phase patterns associated with the transmit events for a given elevation angle (elevation slice) may be selected according to various example embodiments described below. In one example embodiment, the different Fresnel phase patterns are selected to focus the various ultrasound pulses to different spatial regions that are nearby, such that Fresnel focal regions/zone collectively approximate a selected or desired elevation angle and focal depth. As used herein, the phrase "nearby" refers to two focal regions that are overlapping or spatially adjacent, such that the two focal regions both overlap with, or are proximal to, a selected elevation focus. Accordingly, upon the collection and coherent combining of the receive signals, the corresponding image data is associated with a focal region and elevation angle corresponding to the average of the foci of the ultrasound pulses, while reducing the secondary lobe energy as described above.

Figure 2B:
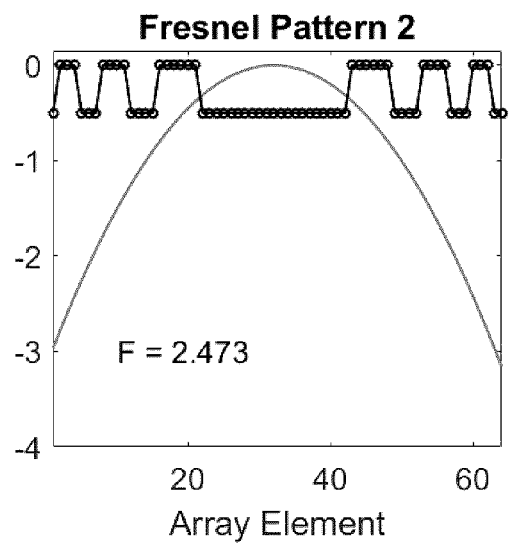
Figure 2C:
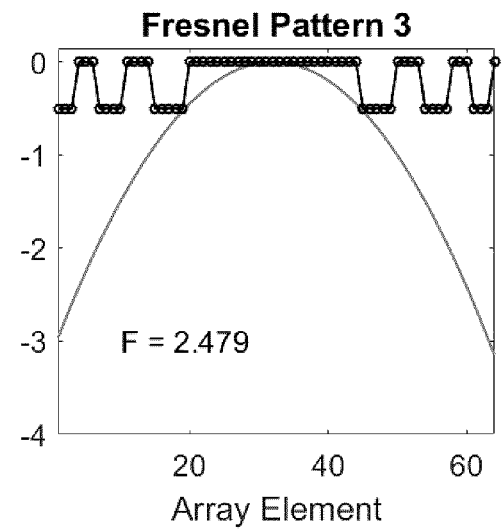

In one example implementation, two or more of the different Fresnel phase patterns may be generated to produce different axial focal depths that are nearby one another, such that the average focal depth corresponds to a desired or selected focal depth. FIGS. 2A-C show three example Fresnel phase patterns according to such an embodiment, in which the different Fresnel phase patterns were generated by moving the focal point down the central axis away from the array.

In another example implementation, two or more of the different Fresnel phase patterns may be generated to produce slightly different elevation angles, such that the average elevation angle of the different elevation angles corresponds to, or approximates, a desired or selected elevation angle. In some example embodiments, two or more of the different Fresnel phase patterns may be generated to produce different axial focal depths, and two or more of the different Fresnel phase patterns may be generated to produce different elevation angles, such that the coherent combining of the receive signals results in the collection of image data corresponding to a desired elevation angle and focal depth (a desired elevation slice of image data).

It will be understood that while it is expected that the reduction of secondary lobes will be maximal when different Fresnel phase patterns are used for each of the transmission events, the present example embodiments may be practiced using at least two different Fresnel phase patterns among the plurality of transmission events.

When multiple Fresnel phase patterns are employed such that the ultrasound pulses from the different transmission events are focused to different depths and/or elevation angles, it is beneficial to apply a group delay (in transmit and receive) to each ultrasound pulse in order to compensate for the different time of flight for each focal region. The value of the group delay may be given by the following equation:

$$del_{group} = \frac{(d_0 - d)}{c}, \quad (3)$$

where d is the distance from the center of the array to the focal zone associated with a given Fresnel pattern of interest involving a spatial offset of the focal zone, do is the baseline distance from the center of the array to a focal zone absent of a spatial offset, and c is the speed of sound in the medium.

Figure 3A:
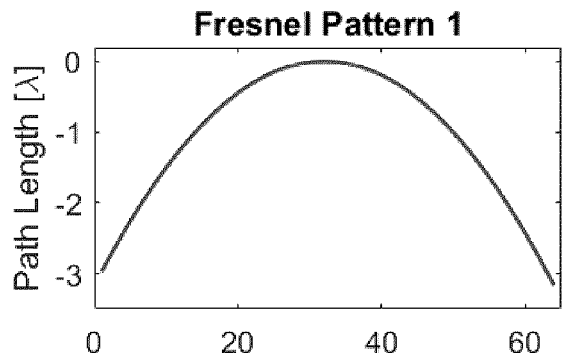
FIGS. 3A-F show examples of different Fresnel phase patterns calculated from the same path length curve, and therefore having a common focus, where the different Fresnel patterns are generated using different phase offsets.
Figure 3D:
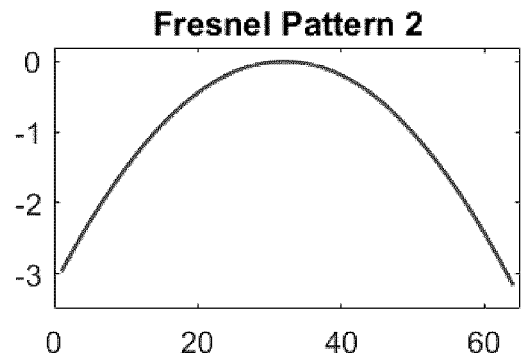
Figure 3B:
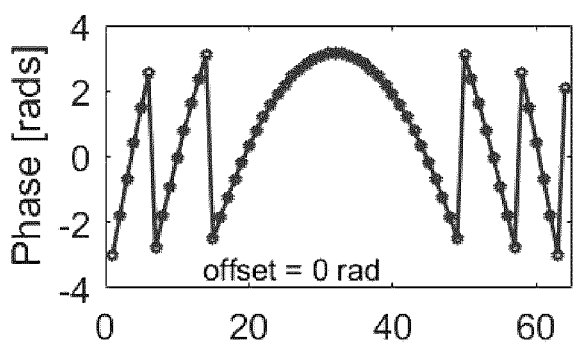
Figure 3E:
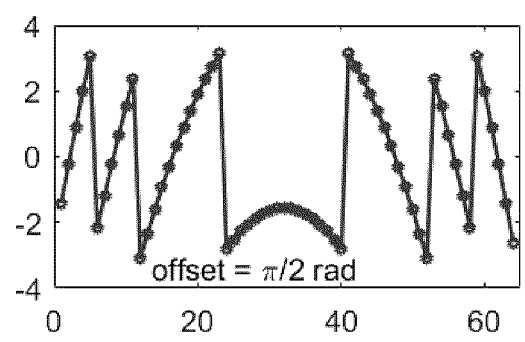
Figure 3C:
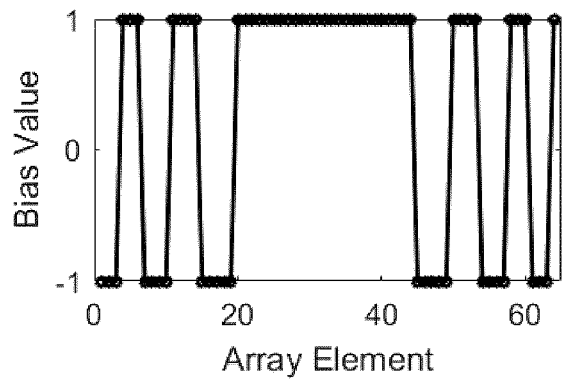
Figure 3F:
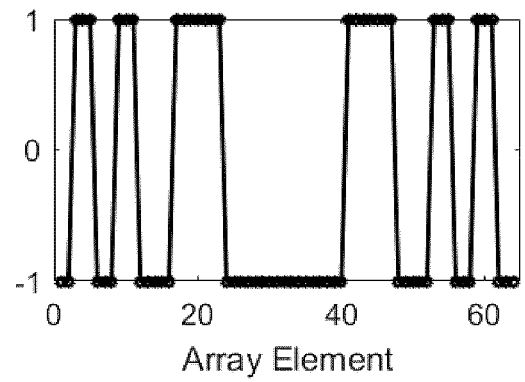

In another example embodiment, the different Fresnel phase patterns can be generated by changing the phase offset value used in the calculation of the Fresnel phase pattern, as an alternative to changing the focal location. An example implementation of such an embodiment is illustrated in FIGS. 3A-3F for an array with 64 elements in the elevation direction. FIGS. 3A-3C illustrate the generation of a first Fresnel phase pattern, and FIGS. 3D-3F illustrate the generation of a second Fresnel phase pattern based on an offset phase. The path length from the focal point to each elevation element is the starting point of calculating the Fresnel pattern, and a common dependence of path length is shown in FIGS. 3A and 3D.

FIGS. 3B and 3E demonstrate the conversion of path length to a phase. Prior to the step of phase wrapping (that is performed according to equation 2) a phase offset is added to the phase profile of FIG. 3B in order to obtain the phase profile shown in FIG. 3E. When this phase offset is changed, as in FIG. 3E, it alters the point that is considered to be the zero phase point and thus produces a different phase wrapped curve after phase wrapping is implemented. This can be clearly seen in FIGS. 3C and 3F, where the phase profiles from FIGS. 3B and 3E are quantized in order to determine the pattern of sign of the bias applied to the array elements, thereby determining the areas of positive bias and areas of negative bias of the Fresnel pattern. As can be seen in FIGS. 3C and 3F, the different phase profiles of FIGS. 3B and 3E yield different Fresnel phase patterns.

In a manner similar to that of the previous example, a group delay may be applied to the array to in order to phase-align the pulses from each Fresnel pattern. The value of the delay for a given Fresnel phase pattern can be obtained by the following equation.

$$del_{group} = \frac{\lambda * \text{offset}}{2\pi \ c}, \quad (4)$$

where λ is the wavelength of the centre frequency of the excitation pulse in the medium, "offset" is the phase offset applied to the phase profile prior to quantization, and c is the speed of sound in the medium.

In some embodiments, the Fresnel phase patterns are employed for receive focusing as well as transmit focusing. In one example implementation, the Fresnel phase pattern employed for a given transmit event may also be applied during the corresponding receive event. In another example implementation, different Fresnel phase patterns may be applied during transmit and receive for a given transmit/receive event.

In some example embodiments, one or more transmit/receive events may be implemented as a sequence of split-aperture events. Accordingly, a given transmit event having a selected Fresnel phase pattern may be implemented as a series of sub-pulses, where each sub-pulse is transmitted using a subset of the array elements, and such that each sub-pulse is generated using a subset of the overall Fresnel phase pattern. An example of such an implementation is shown in FIGS. 4A-4F. Referring to FIGS. 4A-4C, a set of different Fresnel phase patterns are illustrated, each having a spatially perturbed focal location, as per the example method described above. FIGS. 4D-4F show a corresponding set of split-aperture Fresnel phase patterns, where each Fresnel phase pattern is split into four sub-apertures separated by additional path length delays (generated using time delays between sub-aperture transmit and receive events). As can be seen in FIGS. 4D-4F, the additional path lengths are selected to discretely approximate the desired continuous path lengths.

The simulations presented in the examples presented below demonstrate that averaging the receive signals obtained from a plurality of transmit/receive events with multiple Fresnel focusing patterns can lead to a significant reduction of the secondary lobe energy. This reduction is secondary lobe energy can be sufficiently large to enable the use of the present example coherent compounded Fresnel focusing methods for elevation focusing of an ultrasound system having a crossed-array configuration.

However, coherent compounding many times (e.g. 30-100 times) for the elevation focus is not practical if conventional line by line transmit and receive beamforming is employed completed in the azimuth direction. In such a case, the image collection time would be exorbitantly high, as the Fresnel coherent compounding would need to occur repeatedly for each line in the azimuth direction (azimuth dimension).

This problem of high collection times may be solved by combining coherently compounded Fresnel elevation focusing with "plane wave" or "diverging wave" imaging in the azimuth direction. Ultrafast imaging (10,000 frames/s) can be performed using "plane wave" or "diverging wave" imaging because a full 2D image can be collected in a low number of transmit events. The plane wave reaches the entire field of view and dynamic receive beamforming is completed for each spatial location in the frame for every plane wave. Image quality (contrast, SNR, resolution, etc.) is typically improved by emitting multiple plane waves (or diverging waves) and compounding for the same elevation slice. The plane waves are emitted at different angles enabling the creation of a synthetic transmit focus.

According to an example embodiment that is described in detail below, if, for each pulse emission in the sequence of plane waves or diverging waves, the Fresnel pattern is changed by refocusing to a different, yet nearby, spatial location (and/or by employing different phase offsets prior to quantization of the Fresnel phase pattern), the compounding can benefit both planes simultaneously. Prior to describing such example embodiments in further detail, a brief description of the "plane wave" and "diverging wave" imaging methods is henceforth provided.

Azimuthal Imaging Using Coherent Compounded Plane Waves and Diverging Waves

A typical ultrasound system implementing transmit focusing will beamform the emitted phase front so that peak pressure occurs at specific focal depth along a given image line. Receive focusing is then applied to each transmit insonification in order to reconstruct the area of the image window which was most intensely excited during each transmission. Each line is constructed by transmitting to several focal depths so that the acoustic pressure along the given line is relatively constant. A full image window is assembled by linking adjacent lines together. This process requires a high number of insonifications to construct an image window.

Plane wave imaging offers a distinct speed advantage by minimizing the number of insonifications required to generate an image. During receive beamforming, digital focusing is applied to all of the space in the image window, with the result that as few as a single insonification can be employed to generate an image.

In the simple case where a single plane wave is emitted into the medium, there is only a one-way focus on receive, and thus image quality is significantly reduced compared to the conventional image reconstruction previously described. In order to improve the image quality, a transmit focus must be built through successive insonifications. For plane wave imaging the transmit focus is built by coherently compounding plane waves emitted at different angles α, relative to the transmit aperture. Therefore the time between excitation and a point in the medium is given by:

$$\tau_{ec}(\alpha,x,)=(z \cos \alpha + x \sin \alpha)/c, \quad (5)$$

and the receive time back to the transducer at $x_1$ is given by:

$$\tau_{ec}(x_1,x,z)=(z^2+(x-x_1)^2)/c, \quad (6)$$

where $x_1$ is the position of the element on the array. The images generated from each plane wave are then coherently summed to generate a final compounded image. Compounding is the key feature of plane wave imaging which gives it its performance advantage. By exciting the medium from various angles, the interference on receive focusing from objects outside of the focus will not coherently sum together across each frame. This reduces the amount of interference superimposed onto the receive focus.

Figures 5A, 5B, 5C, 5D:
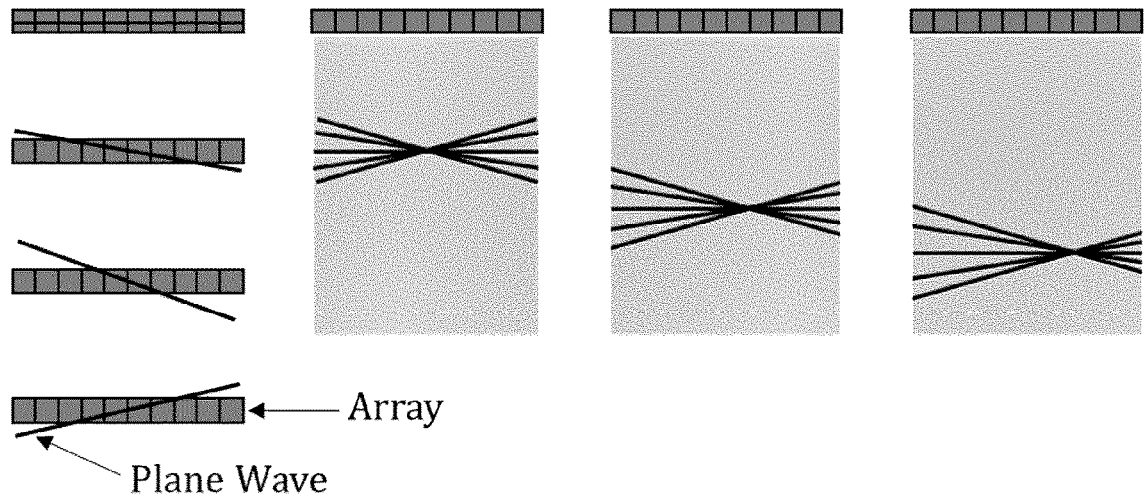
FIGS. 5A-D illustrate the generation of plane waves at a plurality of angles, and the coherent compounding of the plane waves for ultrasound imaging.

FIGS. 5A-D illustrate how a compounding focus can be built from several plane waves emitted at different angles. FIG. 5A illustrates the phasing of a transducer array to generate a plurality of plane waves (the waves would be sequentially generated according to a set of transmit events) having different angles. FIGS. 5B-5D illustrate the coherent compounding of the receive signals collected in response to each plane wave transmit event, in order to generate image data for different image foci. It has been found that images created from plane wave compounding can exhibit image improvements, matching and in some respects exceeding conventional beamforming techniques. For linear arrays, it has been shown that plane wave imaging yields benefits for contrast, SNR, and lateral resolution, while achieving higher frame rates.

Figures 6A, 6B, 6C, 6D:
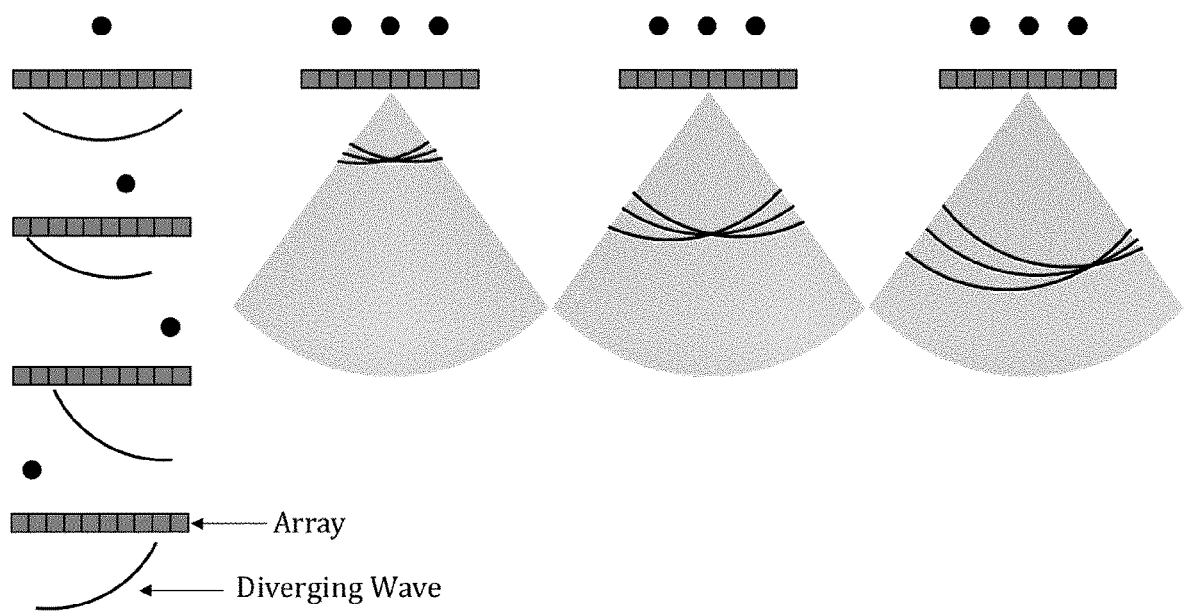
FIGS. 6A-D illustrate the generation of diverging waves having a plurality of virtual foci, and the coherent compounding of the diverging waves for ultrasound imaging.

Diverging waves can also be used as an alternative to plane wave imaging. This imaging technique can generate an image from a single insonification, similar to the plane wave imaging modality described above. In order to produce diverging waves, the elements on the array are excited to mimic a virtual point source behind the imaging array. As in the preceding example case of plane wave imaging, the image quality is improved by coherently compounding images generated from different virtual point source positions behind the array. The generation of diverging wavefronts having different virtual point source locations is illustrated in FIG. 6A. The different wavefronts can be coherently compounded, as shown in FIGS. 6B-6D, in order to perform receive focusing at different focal locations.

Although the preceding two example embodiments employed plane waves and diverging spherical waves, respectively, it will be understood that any transmit wave shape can be used for compounding, provided that the geometry of the wavefront is suitably accounted for during receive focusing.

Combined Coherent Compounded Azimuth Plane Wave/Diverging Wave Imaging with Coherent Compounded Elevation Fresnel Focusing In some example embodiments, the aforementioned method of performing coherently compounded Fresnel elevation focusing may be advantageously implemented in combination with 'plane wave' or 'diverging wave' (or an unfocused or defocused wave having a controlled wavefront shape) imaging in the azimuth direction, in order to achieve volumetric imaging in an efficient manner. In one example embodiment, a crossed-electrode transducer array may be employed to perform coherently compounded volumetric imaging, where coherently compounded plane wave or diverging wave imaging is employed for the collection of a two-dimensional image slice, and where the elevation angle of the image slice is controlled using coherently compounded Fresnel focusing.

For example, a sequence of plane waves or diverging waves may be transmitted and received using an azimuth electrode array of a crossed-electrode array, where the wavefronts of the waves are configured for coherent compounded imaging, and elevation electrodes of the crossed-electrode array may be employed to apply bias voltages for Fresnel focusing at a selected elevation angle, such that different Fresnel phase patterns are applied during different transmit events, thereby reducing the elevation secondary lobe energy as described above.

As explained above, the crossed-electrode array is formed from a first set of electrodes and a second set of electrodes, where an array of ultrasound elements are defined between the first and second electrode arrays. The first set of electrodes are spaced along, and extend perpendicular to, an azimuth direction, such that the first electrode array is suitable for imaging in the azimuth direction. The electrodes of the second electrode array are spaced along, and extend perpendicular to, the elevation direction, such that the second electrode array is suitable for imaging in the elevation direction. The ultrasound array elements are formed such that the phase of the ultrasound waves emitted from the array is dependent on the polarity of a bias voltage applied by the second electrode array.

Figure 7:
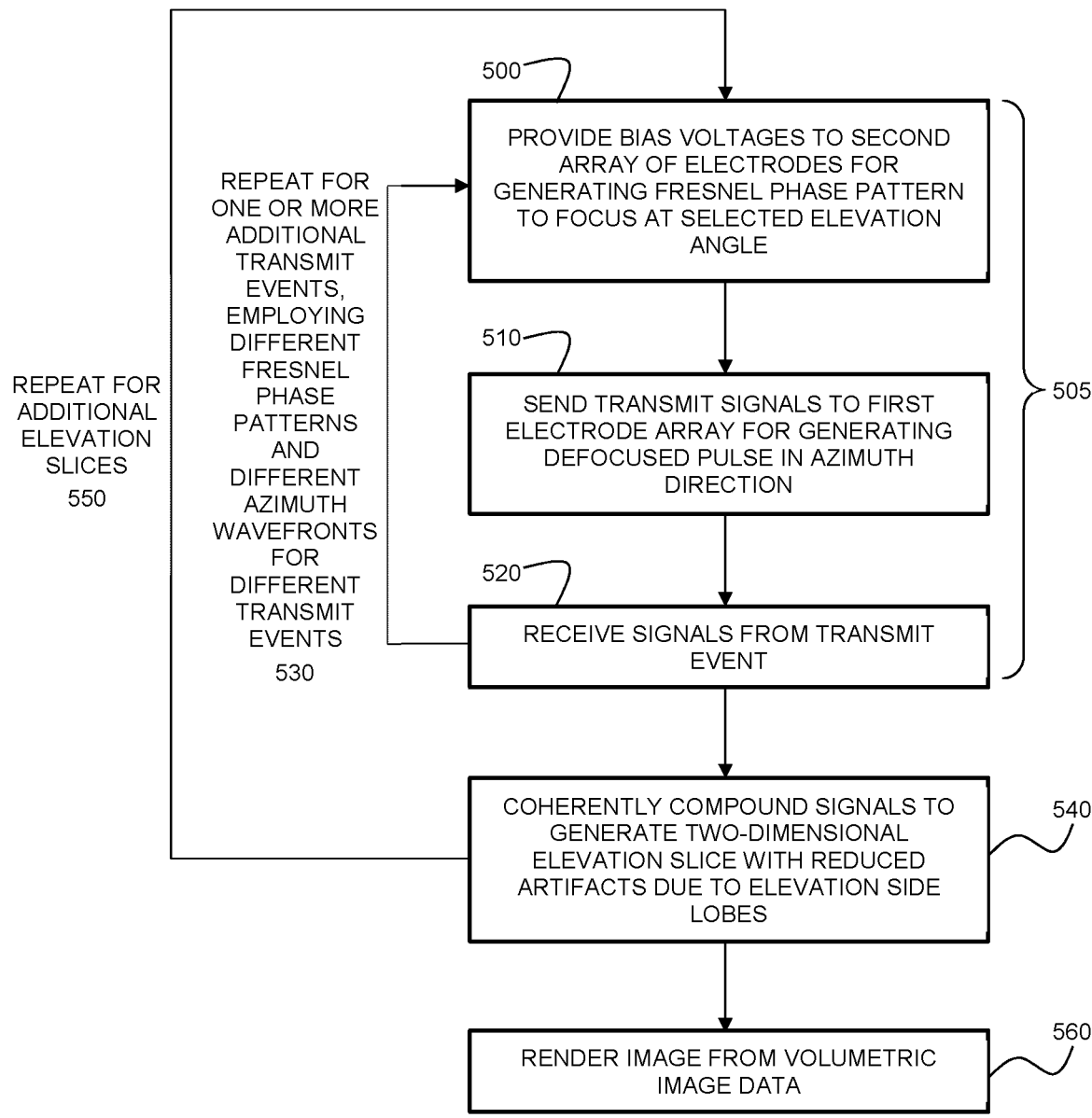
FIG. 7 is a flow chart showing an example method of performing imaging with a crossed-electrode transducer based on coherently compounded Fresnel focusing in the elevation direction and linear or diverging wave coherently compounded beamforming in the azimuth direction.

As illustrated in the flow chart provided in FIG. 7, volumetric imaging is performed with the cross-electrode ultrasound array by collecting image data from a set of two-dimensional image slices, with each two-dimensional image slice corresponding to a different elevation angle. Each two-dimensional image slice is collected using coherent compounded plane/diverging wave imaging (coherent compounding using plane waves or diverging waves).

As shown at 505 and 530, a series of transmit/receive events 505 are performed in order to collect image data corresponding to a first elevation slice. Instead of performing a single transmit/receive, a sequence of transmit/receive events are performed in order to facilitate coherent compounded imaging. Each transmit/receive event 505 is performed by applying a set of bias voltages to the second electrode array (as shown at 500) and sending a set of transmit signals to the first electrode array (as shown at 510). The resulting reflected or scattered ultrasound waves are detected as receive signals at 520. As shown at 500, the bias voltages are applied in order to generate a Fresnel phase array, such that the emitted ultrasound pulse is focused in the elevation direction at the elevation angle corresponding to the initial elevation slice. Furthermore, as shown at 510, the transmit signals are sent to the first electrode array in order to generate a defocused pulse (e.g. a linear phase front—analogous to a plane wave, or a diverging—e.g. circular—wavefront).

As shown at 530, steps 500-520 are repeated for one or more additional transmit events, where different Fresnel phase patterns are employed for different transmit/receive events in order to reduce the effect of elevation secondary lobe energy on the resulting image data. The transmit signals are provided to the first electrode array such that the wavefronts associated with the different transmit events are suitable for performing coherent compounded imaging in the azimuth direction. The different Fresnel phase patterns are provided such that the sequence of ultrasound pulses associated with a given elevation slice are focused at or near a common focal region. For example, as described above, the transmitted ultrasound pulses may be focused by the various Fresnel phase patterns such that the ultrasound pulses are in close proximity, but are sufficiently spatially separated such that the quantized Fresnel phase patterns are different. Additionally or alternatively, as described above, the different Fresnel phase patterns may have with a common focus, but may be generated with different phase offsets prior to quantization, such that the quantized Fresnel phase patterns are different. As noted above, it is preferable to apply group delays to the different transmit pulses when different Fresnel phase patterns are employed, such that group delay variations due to Fresnel phase patterns having different associated focal locations or different phase offsets can be suitably compensated. Compensation of these group delays is performed in the azimuth plane when performing coherent compounding of the defocused azimuth plane wavefronts.

In step 540, the receive signals detected from the first electrode array for the different transmit/receive events are coherently compounded in order to generate two-dimensional elevation image slice data. As explained above, the use of the different Fresnel patterns facilitates the reduction of the contribution of elevation secondary lobe energy to the elevation image slice data.

The aforementioned steps (500-540) may then be repeated one or more times, as shown at 550, in order to collect image data corresponding to a plurality of elevation slices, thereby generating a set of volumetric image data. As shown at 560, the volumetric image data may then be processed to render one or more images.

It is noted that the flow chart shown in FIG. 7 is provided as a non-limiting illustrative example of a method of performing volumetric imaging using coherently compounded Fresnel elevation focusing and azimuth imaging, and modifications may be made to the steps shown in the flow chart without departing from the intended scope of the present disclosure. For example, the coherent compounding of the receive signals (shown at 540) need not occur immediately after collecting the receive signals for a given elevation angle, and may instead be performed, on a per-slice basis, after having collected the receive signals from the plurality of elevation slices.

This method shown in FIG. 7 has the advantage of employing simultaneous compounding in two-dimensions, thereby improving image quality in both dimensions while facilitating high volumetric frame rates. It has been found that this method, and variations thereof, may enable the rapid collection of two-dimensional elevation slices, thereby facilitating the ultrafast collection of volumetric image data. For example, in some example implementations, each two-dimensional image slice may be collected in less than 1.25 ms. It is noted that the time to collect a multi-slice volumetric image data set depends on how many slices are desired or required.

Figure 8:
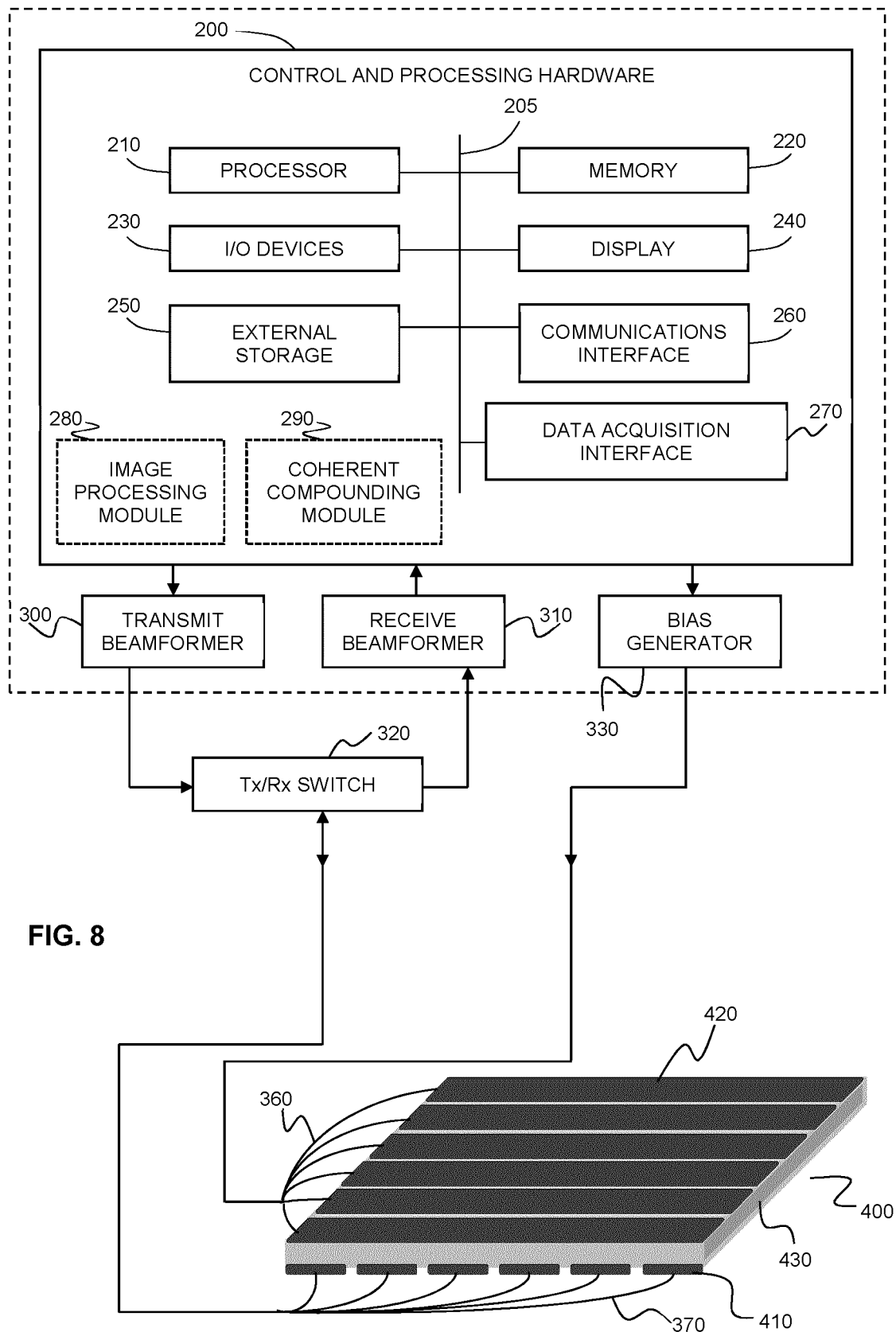
FIG. 8 illustrates an example imaging system for performing imaging with a crossed-electrode transducer based on coherently compounded Fresnel focusing in the elevation direction and linear or diverging wave coherently compounded beamforming in the azimuth direction.

Referring now to FIG. 8, an example imaging system is illustrated for performing imaging with a crossed-electrode transducer based on coherently compounded Fresnel focusing in the elevation direction and linear or diverging wave coherently compounded beamforming in the azimuth direction. The example system includes a crossed-electrode ultrasound transducer 400 (which may be a component of an ultrasound imaging device, such as an ultrasound imaging endoscope), a transmit beamformer 300 with pulser-receiver circuitry 320, a receive beamformer 310, a bias generator 330, and control and processing hardware 200 (e.g. a controller, computer, or other computing system).

Control and processing hardware 200 is employed to control transmit beamformer 300 and receive beamformer 310, and for processing the beamformed receive signals. As shown in FIG. 8, in one embodiment, control and processing hardware 200 may include a processor 210, a memory 220, a system bus 205, one or more input/output devices 230, and a plurality of optional additional devices such as communications interface 260, display 240, external storage 250, and data acquisition interface 270.

An example of crossed electrode ultrasound transducer 400 is disclosed in US Patent Application No. US 2007/0079658 (Wagner), titled "ROTATING APERTURE FOR ULTRASOUND IMAGING WITH A CAPACITIVE MEMBRANE OR ELECTROSTRICTIVE ULTRASOUND TRANSDUCER". In FIG. 8, another example of a crossed-electrode ultrasound transducer is shown including, on either side of an electrostrictive layer 430, a first array of first electrodes 410 and a second array of second electrodes 420. First electrodes 410 extend in a first direction, and second electrodes 420 extend in a second direction. First electrodes 410 are employed for focusing ultrasound energy in a first plane that is perpendicular to an emitting surface of the ultrasound transducer, and includes the first direction. Second electrodes 420 are employed for focusing ultrasound energy in a second plane that is perpendicular to an emitting surface of the ultrasound transducer, and includes the second direction. The first and second planes may be perpendicular in order to enable scanning in orthogonal directions (e.g. azimuth and elevation).

In the present example implementation, first electrodes 410 and second electrodes 420 are shown in a perpendicular crossed configuration, although in other example implementations, the electrodes can be provided in a crossed configuration with an angle of other that 90 degrees. Furthermore, although the figure shows the first and second electrodes as longitudinal electrodes, it will be understood that the electrodes need not be strictly linear in shape, provided that the first electrodes extend in the first direction and the second electrodes extend in the second direction and define linear arrays of ultrasound elements in two dimensions.

It will be understood that although the figure shows an example implementation involving an unkerfed layer of electrostrictive material as the ultrasound transduction layer. Although such an embodiment, in which a crossed electrode array formed by defining electrodes on the top and bottom surface of a monolithic piezoelectric, may be readily fabricated, this approach may result in substantial mechanical crosstalk between elements, thereby reducing the directivity and the quality of the radiation pattern.

In other example embodiments, other materials and configurations may be employed to form a crossed-electrode array in order to reduce mechanical crosstalk. For example, kerfs may be cut or otherwise formed between the elements in one dimension (kerfed in one direction/dimension and kerfless in the other direction/dimension) or two dimensions of the array, or the piezoelectric substrate can be replaced with a composite piezoelectric substrate (e.g. a matrix of pillars embedded in an epoxy). A kerfed array may be formed as a semi-kerfed array, where an electrorestrictive ceramic is cut only partially through the thickness. Alternatively, a crossed-electrode array may be formed as an array of capacitive micromachined ultrasound transducers, which, like a kerfed or unkerfed electrostrictive substrate, are capable of acoustic transduction upon the application of a bias voltage, such that the ultrasound energy is emitted upon the application of voltage pulses when the bias voltage is present.

Referring again to the example embodiment illustrated in FIG. 8, the first array of first electrodes 410 are in electrical communication with the transmit beamformer 300 via the Tx/Rx switch 320 and conductors 370, and such that transmit voltage pulses are provided to the first array of first electrodes for generating a set of defocused ultrasound pulses for performing coherent compounded imaging in the azimuth direction. Furthermore, during transmit, the bias generator 330 applies biases to the second array of second electrodes 420 via conductors 360, such that the ultrasound pulse is focused within the second plane via a Fresnel aperture, and such that the Fresnel phase patterns change among multiple transmit events, as described above.

The present example methods of performing two-dimensional coherently compounded imaging (e.g. the example method illustrated in FIG. 7) can be implemented via processor 210 and/or memory 220. As shown in FIG. 8, the control of the Fresnel phase patterns and the control of the timing of transmit/receive events associated with the compounded coherent imaging in the azimuth direction, may be implemented by control and processing hardware 200, via executable instructions represented as coherent compounding module 290. The control and processing hardware 200 may include and execute scan conversion software (e.g. real-time scan conversion software).

The functionalities described herein can be partially implemented via hardware logic in processor 210 and partially using the instructions stored in memory 220. Some embodiments may be implemented using processor 210 without additional instructions stored in memory 220. Some embodiments are implemented using the instructions stored in memory 220 for execution by one or more general purpose microprocessors. In some example embodiments, customized processors, such as application specific integrated circuits (ASIC) or field programmable gate array (FPGA), may be employed. Thus, the disclosure is not limited to a specific configuration of hardware and/or software.

Referring again to FIG. 8, it is to be understood that the example system shown in the figure is not intended to be limited to the components that may be employed in a given implementation. For example, the system may include one or more additional processors. Furthermore, one or more components of control and processing hardware 200 may be provided as an external component that is interfaced to a processing device. For example, as shown in the figure, any one or more of transmit beamformer 300, receive beamformer 310, and bias generator 330 may be included as a component of control and processing hardware 200 (as shown within the dashed line), or may be provided as one or more external devices. Transmit beamformer 300, receive beamformer 310, image processing module 280, and coherent compounding module 290 may be configured or programmed to execute algorithms for performing the methods described herein.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed herein can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices. As used herein, the phrases "computer readable material" and "computer readable storage medium" refers to all computer-readable media, except for a transitory propagating signal per se.

The present example embodiments that employ a crossed-electrode configuration provide significant benefits over conventional 2D array designs. The crossed-electrode array need only employ 2N electrical connections and only N beamforming channels, because the top electrodes provide the active lens control in the elevation plane. The alternative approach to capturing 3D image volumes with a conventional 2D array requires $N^2$ elements and beamforming channels. The low beamforming complexity and minimal electrical connectivity therefore provides significant practical advantages over conventional 2D array designs. This aspect can be advantageous in some applications that require miniaturized packaging, because the electrical interconnect is a significant fraction of the packaging, and therefore minimizing the number of elements required is important for miniaturization.

As described above, acoustic waves, like light, can be focused using a Fresnel lens or zone plate approach. Fresnel zone plates can produce a tight focus, especially when using a large aperture. A Fresnel type approach is implemented by controlling the pulse polarity across an ultrasound transducer. Alternatively, a pattern of positive and negative pulses can be set to mimic a steered plane wave insonification. The control over pulse polarity can be achieved using a piezoelectric substrate whose response depends on a DC bias (i.e. electrostrictive ceramic, CMUTs) in place of conventional piezoelectric. This type of material is only piezoelectrically active while a bias voltage is applied. In addition, the response is tunable with the amplitude of the bias voltage. When no voltage applied to the transducer, the response is negligible, and when a DC bias is applied, the phase of the acoustic wave produced is quantized to either +90 or −90 degrees, depending on whether the bias is positive or negative. Therefore, the emitted wave front from a substrate can be dynamically altered (focused, steered) by only changing a series of positive and negative biases along the substrate. This is a powerful concept because an ultrasound image could be formed using only a single RF data channel and a sequence of biases across a piezoelectric substrate.

Figure 14A:
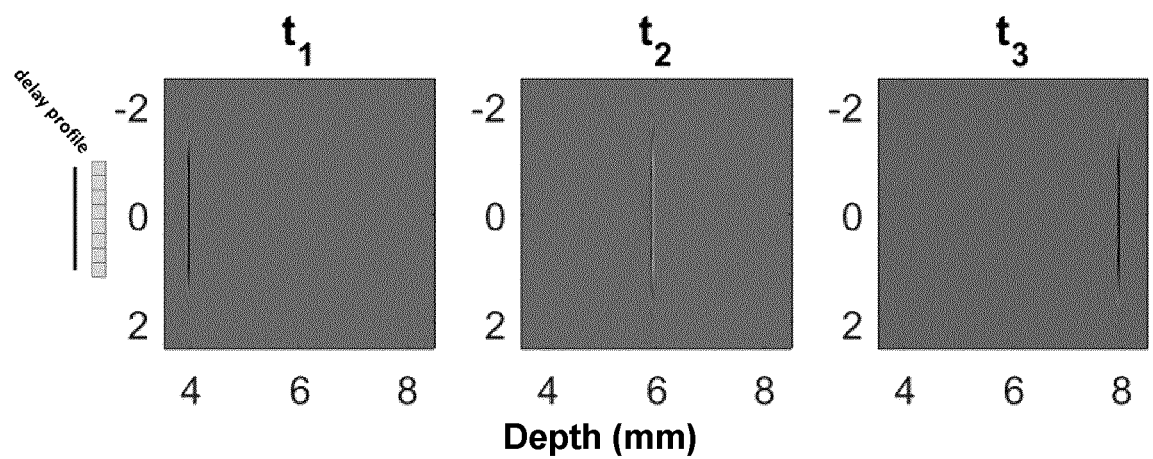
FIGS. 14A-14O show simulations of the propagating pressure wave at three points in time for (A) a plane wave transmission, (B) an angled plane wave and (C), (D) bias controlled Fresnel wave examples.
Figure 14B:
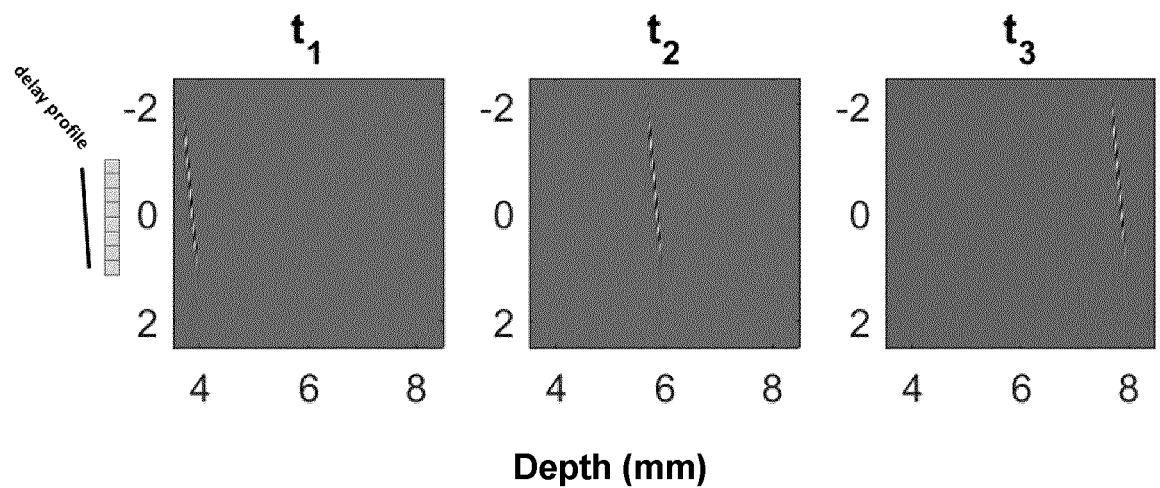

As described above, a plane wave insonifies a whole image region in one transmit event by pulsing all elements of an ultrasound array at the same time. Ultrafast imaging (10,000 frames/s) can be completed with plane wave imaging because a whole 2D image can be collected in one transmit event. The plane wave reaches the entire field of view and dynamic receive beamforming is completed for each image pixel location in the frame for every plane wave. Image quality (contrast, SNR, resolution, etc.) is typically improved by emitting multiple plane waves (or diverging waves) and coherently compounding each frame. The plane waves are emitted at different angles enabling the creation of a synthetic transmit focus. Examples of the generation of such plane waves are illustrated in FIGS. 14A and 14B.

Figure 14C:
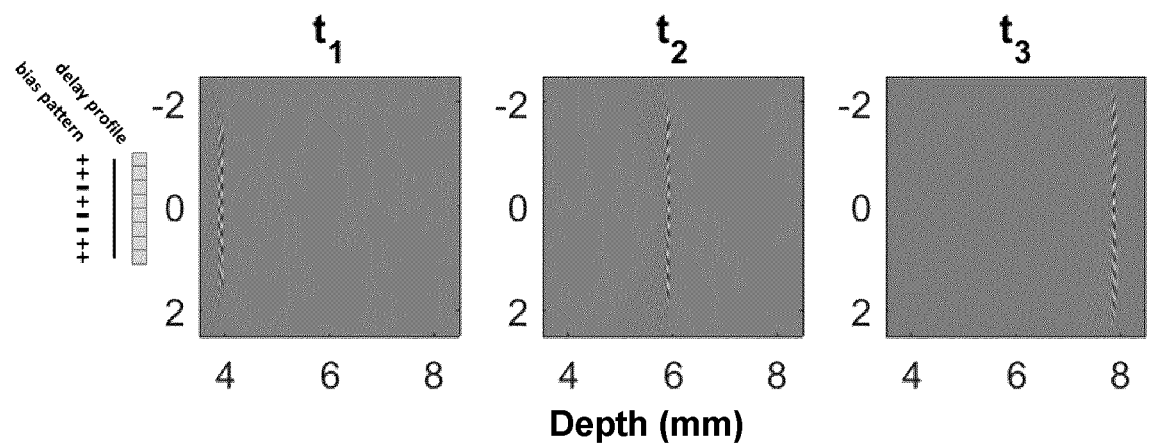
Figure 14D:
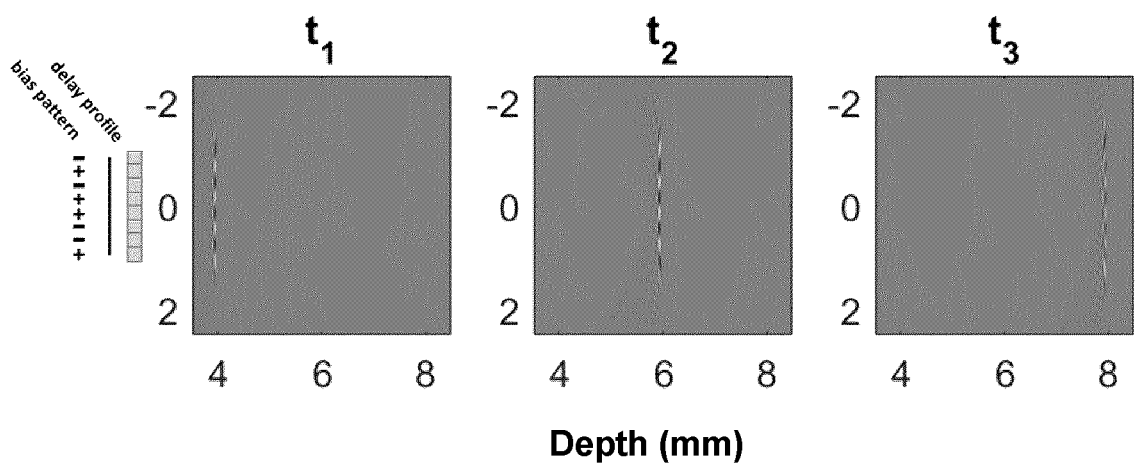

Instead of producing a flat plane wave, a pattern of biases across the array can produce an uneven/irregular wave front. Such wavefronts, generated by a bias pattern that quantizes the phase of the emitted ultrasound waves according to one of two polarities, are henceforth referred to as defocused Fresnel waves. Examples of the generation of such wavefronts are provided in FIGS. 14C and 14D. These propagating waves can be used in the same way as plane waves to perform fast imaging. Coherently compounding the results of a series of these bias controlled Fresnel waves can improve image quality in the same way as in plane wave imaging. To coherently compound each frame that transmits a different, irregular wave front the phase at each of the image pixel locations must be known and used in the synthetic transmit beamforming. This requires simulating the wave front throughout the image region and creating a look up table of phase offsets from one image to the next.

When a true plane wave is used to image, this calculation is simple because the wave front begins and remains in-phase as it travels.

If just a single RF channel is used, the receive data must be separated in such a way as to isolate the information coming from each element of the array. One option to achieve such separation of receive data is to only activate a single element on receive (one element biased while all the others are grounded), and then to repeat the same transmit bias pattern, moving the active receive element along the array. This process is repeated for each biased element in the array. With the RF data from each individual element, a synthetic receive aperture can then be formed. The main disadvantages to this approach are the reduced SNR when using a single receive array element and the increased time required to generate an image (increased by a factor of the number of elements, N).

However, in some example embodiments, Hadamard encoding can be used for the receive patterns. A Hadamard matrix is made up of entries equal to +1 or −1 with the property that each row is mutually orthogonal. An example of a 16×16 Hadamard matrix is provided in FIG. 15.

When the receive bias pattern is Hadamard encoded, a matrix calculation can be performed to decode and retrieve the equivalent of the RF data from each element across the array, as shown below, using the properties of orthogonal matrices. In the equation below, the Hadamard matrix is given by H, the column vector of RF data at time t received for each coded receive bias pattern is given by R and the decoded RF data at time t for each element is given by E. This approach still requires the additional transmit events (N events, one for each element of the bias pattern, e.g. for each electrode of an electrode array establishing the bias pattern), and all elements are active on receive in order to detect the encoded receive signals.

$$H^{-1} R(t) = E(t) \quad (7)$$

$$R(t) = \begin{bmatrix} RF_{rx1} \\ RF_{rx2} \\ \vdots \\ RF_{rxN} \end{bmatrix}_t, \quad E(t) = \begin{bmatrix} RF_{ele1} \\ RF_{ele2} \\ \vdots \\ RF_{eleN} \end{bmatrix}_t$$

In one example embodiment, Hadamard receive encoding may be employed to perform two-dimensional imaging with a one-dimensional array of bias electrodes, and a single signal electrode. According to such an example embodiment, a dynamically varied bias pattern on a bias sensitive electro-restrictive element (generated by an array of bias electrodes) can be applied to generate two-dimensional images over multiple pulses and Hadamard encoded bias patterns. Such an approach can result in a significant reduction in the required number of RF analog channels, which may provide benefits such as simplifying the electronic hardware and associated cost, and reducing the cabling system dimensionally for catheter-based (or probe-based) imaging applications.

Figure 16A:
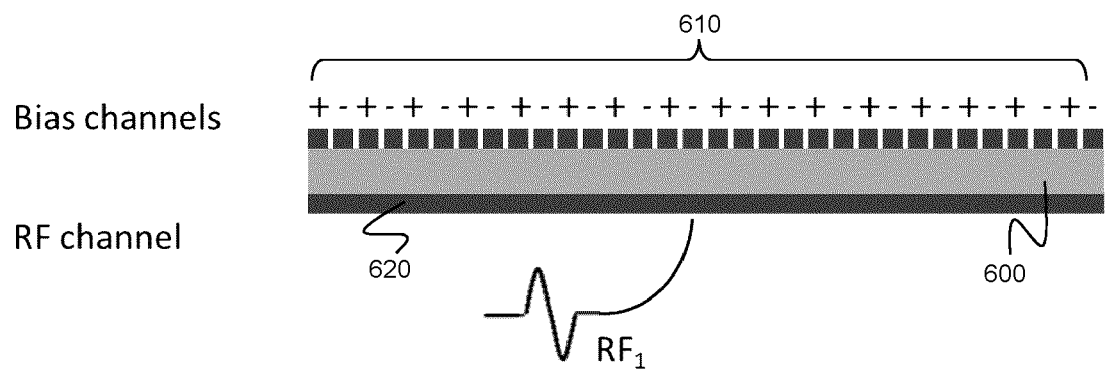
FIGS. 16A and 16B illustrate an example embodiment in which two-dimensional imaging is performed with bias control across an element and (A) a single RF signal channel, and (B) multiple RF signal channels, with each channel forming a sub-aperture of bias electrodes.

As noted above, a high-quality radiation pattern can be generated with a linear element connected to only a single RF channel as long as the DC bias polarity can be varied and dynamically changed across the element over multiple pulses. An example of such a configuration is shown in FIG. 16A. The figure shows a piezoelectric substrate 600 whose response depends on a DC bias (i.e. electrostrictive ceramic, CMUTs), where a one-dimensional array of bias electrodes 610 is formed on one side of the substrate, and a single signal (RF) electrode 620 is formed on the opposing side. Bias voltages are applied to the bias electrodes 610, which in turn bias the piezoelectric substrate 600 to control the (quantized) polarity of the acoustic phase of emitted ultrasound.

Such an array may be employed according to several example embodiments that employ dynamic one-dimensional bias patterns for two-dimensional imaging. In one example embodiment, the one-dimensional ultrasound array is employed to transmit defocused Fresnel wave, with multiple transmit pulses per defocused Fresnel wave, and receive Hadamard encoding is employed, with a different Hadamard matrix row being employed for receive encoding each transmitted pulse of a given defocused Fresnel wave. The Hadamard decoded receive signals may then be coherently compounded to generate a two-dimensional image.

In another example embodiment, the bias electrode array may be employed to transmit a focused Fresnel wavefront, where several pulses are transmitted per image line (angle), and receive Hadamard encoding is employed to decode the receive signals, where a different Hadamard matrix row is employed to receive encode each pulse for a given image line. The Hadamard decoded signals, for a given image line angle, may be subsequently employed to generate an image line via dynamic receive beamforming. This process may be repeated for a plurality of image lines in order to generate two-dimensional image data.

The aforementioned example two-dimensional Hadamard encoding embodiments may be applied to three-dimensional imaging, as described further below.

It is noted that a trade-off, which inherently results from generating two-dimensional images with a linear element connected to a single RF channel with varied and dynamically changing bias patterns across the element, is a significant reduction in frame rate relative to conventional techniques that have direct access to RF channel data from multiple array elements. For example, in the preceding example embodiment involving the transmitting of a Fresnel focused beam in combination with receive Hadamard encoding, the transmit focus is repeated 'N' times where 'N' is the number of bias channels across the element employed for Hadamard encoding. The present inventors have found that in such an embodiment, in order to achieve high-quality imaging and to avoid grating lobe artifacts, a minimum of approximately 64 bias channels is beneficial. With 64 bias channels, 64 transmit pulses per image line would be required to effectively decode the Hadamard matrix and obtain channel data for 64 channels. With this large number of pulses, high frame rate imaging would be difficult to achieve at present (frame rate='N'×no. of lines).

Alternatively, using the other example embodiment involving transmitting with defocused Fresnel wave and Hadamard encoding the received signals, 'N' pulses of identical plane waves would be required for each pre-compounded frame to decode and obtain channel data on receive. If high quality images are desired, it may be beneficial to include at least 40 compounds, again making high frame rate imaging challenging given the presently available technology (frame rate='N'×no. of compounds).

Figure 16B:
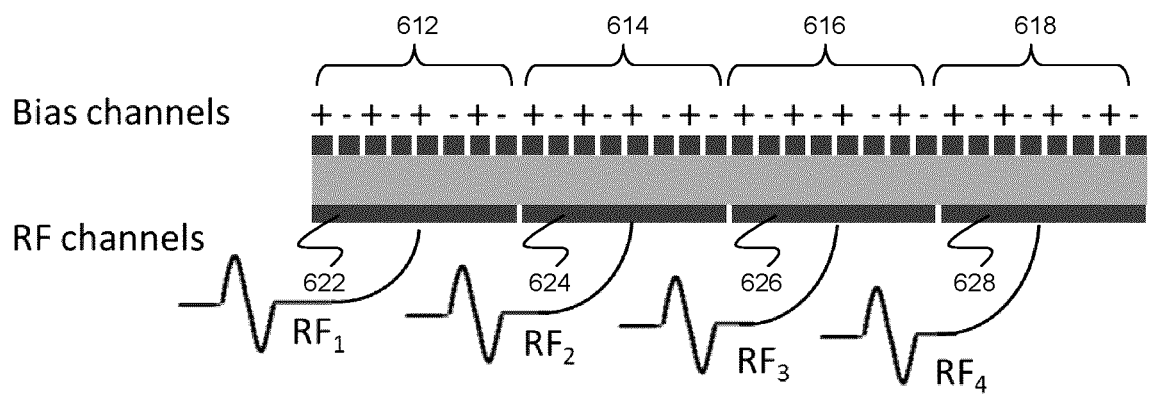

In another example embodiment, the trade-off between the number of channels and frame rate can be adjusted by employing a number of RF signal channels that is greater than 1, and where the number of bias electrodes is greater than the number of signal electrodes (channels). For example, the number of signal channels may be 2, 3, 4, 5, 6, 7 or 8. An example of a four-signal-electrode configuration is shown in FIG. 16B. As shown in the figure, array is broken into four RF signal apertures, having respective signal electrodes 622, 624, 626 and 628, and respective sets of bias electrodes 612, 614, 616 and 618. For example, if N=64 total bias channels are employed and are broken into 4 sub-apertures, four Hadamard matrices are employed, each with 16 channels, and the frame rate is increased by a factor of 4 relative to the single signal channel embodiment.

For example, according to the embodiment that involves the transmission of a Fresnel focused beam in combination with received Hadamard encoding, the entire aperture (or a portion thereof) could be employed for Fresnel transmit focusing, but the receive encoding would be performed on a per-sub-aperture basis. The number of transmitted pulses, per image line, would be equal to the number of bias electrodes in each sub-aperture, instead of the number of bias electrodes across the full aperture. The decoded channel data from the sub-apertures may then be dynamically receive beamformed along the image line, and repeated for multiple image lines. The frame rate for such an embodiment would therefore be: frame rate=N/(no. sub apertures)× no. of lines.

Alternatively, according to the embodiment that employs the transmission of defocused Fresnel wave in combination with Hadamard receive encoding, the entire aperture (or a portion thereof) could be employed for the transmission of defocused Fresnel wave, but the receive encoding would be performed on a per-sub-aperture basis. The number of transmitted pulses, per defocused Fresnel wave, would be equal to the number of bias electrodes in each sub-aperture, instead of the number of bias electrodes across the full aperture. The frame rate for such an embodiment would be: frame rate=N/(no. sub apertures)×no. of compounds.

It is noted that embodiments described herein may be employed for substrates that are kerfed, kerfless where the electrodes are on a monolithic piezo, and kerfless where the electrodes are on a composite piezo. The aforementioned methods that involve Hadamard encoding, which have been illustrated in the non-limiting example of two-dimensional imaging with a one-dimensional array of bias electrodes (and one or more single electrodes/channels) may be applied to three-dimensional imaging using a two-dimensional crossed-electrode array. As described above, the crossed electrode array may be formed using of a linear set of electrodes on the top of a piezoelectric substrate and an equal but orthogonal set of electrodes on the bottom. Crossed electrode arrays address some of the challenges in 3D ultrasound imaging, especially a huge reduction in number of elements compared to a grid array. However, creating a two-way focused volumetric image in real-time is difficult with these arrays because azimuth and elevation dimensions cannot be beamformed at the same time.

As described below, in some example embodiments, one of the two electrode arrays of the crossed electrode may be employed for the generation of defocused Fresnel wave or a Fresnel focused pulse upon transmit in the elevation direction, and this electrode array can be employed for Hadamard receive encoding. The other electrode array may be employed for azimuth imaging. In some example embodiments, the second array may be employed for coherent compounding in the azimuth direction, and the coherent compounding may be performed in parallel (e.g. simultaneously with) with the multiple pulse transmission and reception operations required for Hadamard encoding in the elevation direction.

Figure 24:
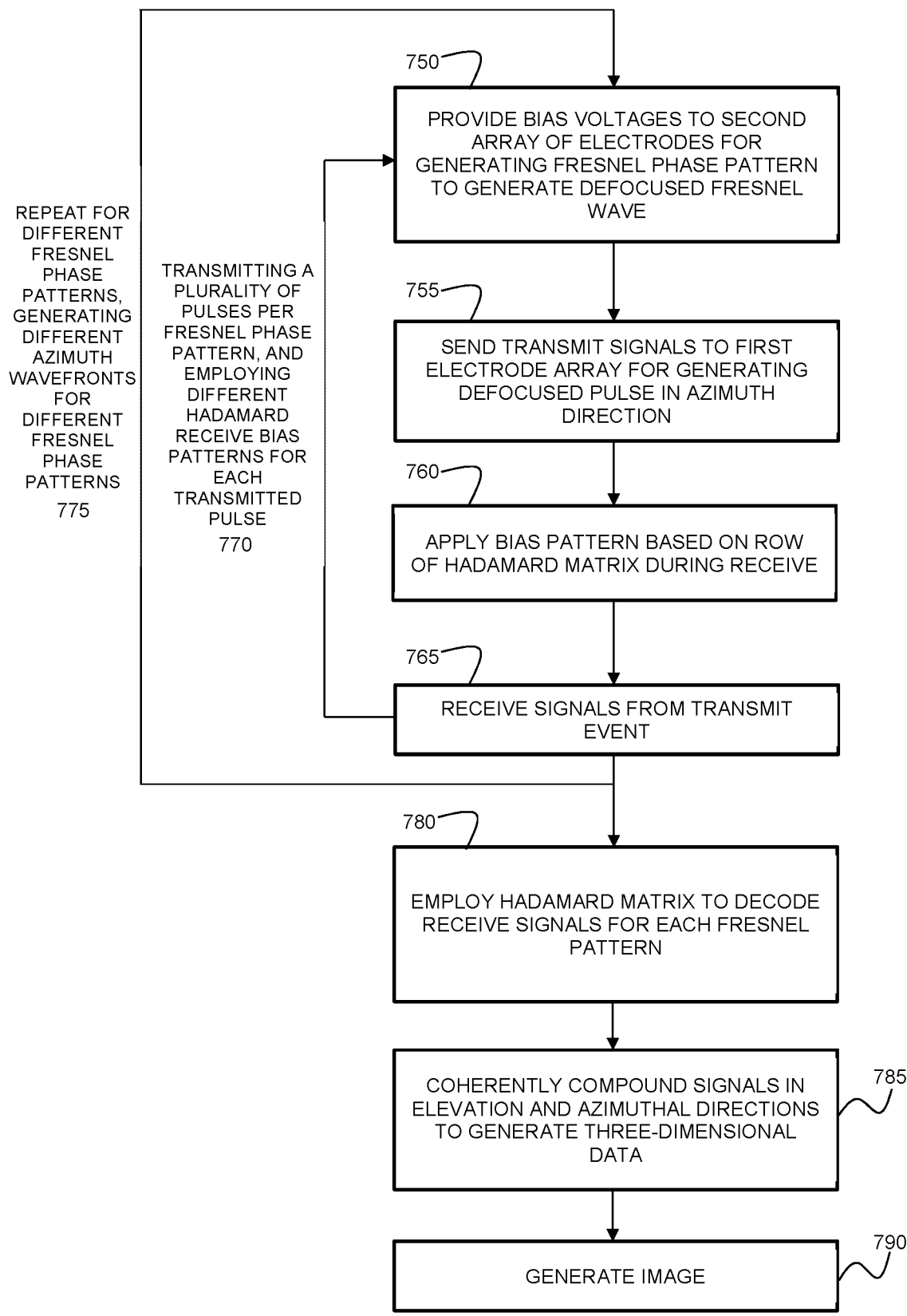
FIG. 24 is a flow chart illustrating an example method of performing three-dimensional imaging using a crossed-electrode array, in which defocused Fresnel waves are employed upon transmit, and Hadamard encoding is employed upon receive in the elevation direction, in parallel with coherent compounding in the azimuthal direction.

In one example embodiment, a crossed-electrode array may be employed such that bias-controlled defocused Fresnel wave are employed in the elevation direction (as described in the previous one-dimensional example embodiment) while conventional imaging (i.e. B-mode, plane wave or diverging wave imaging) may be performed in the azimuth direction, where the compounding that is performed for the defocused Fresnel wave can benefit both planes simultaneously. For example, in the case that coherent compounding of defocused waves is employed in both the elevation and azimuth directions, this compounding can be performed in parallel. The number of transmit events required to build a 3D image in this case depends on the number of compounds necessary to achieve suitable image quality and the number of elevational elements of the crossed electrode array. By using Hadamard encoding on receive for the elevation direction, then N compounds would be completed, per defocused Fresnel wave, in order to properly decode and build the synthetic receive aperture, where N is the number of bias electrodes that are employed for Hadamard encoding. In such as case, the frame rate would be: frame rate=PRF/[N*FW] where PRF is the pulse repetition frequency and FW is the number of defocused Fresnel waves. Azimuth compounding is performed simultaneously and so does not influence frame rate. FIG. 24 provides a flow chart illustrating an example implementation of this method, showing steps 750-790.

Figure 23:
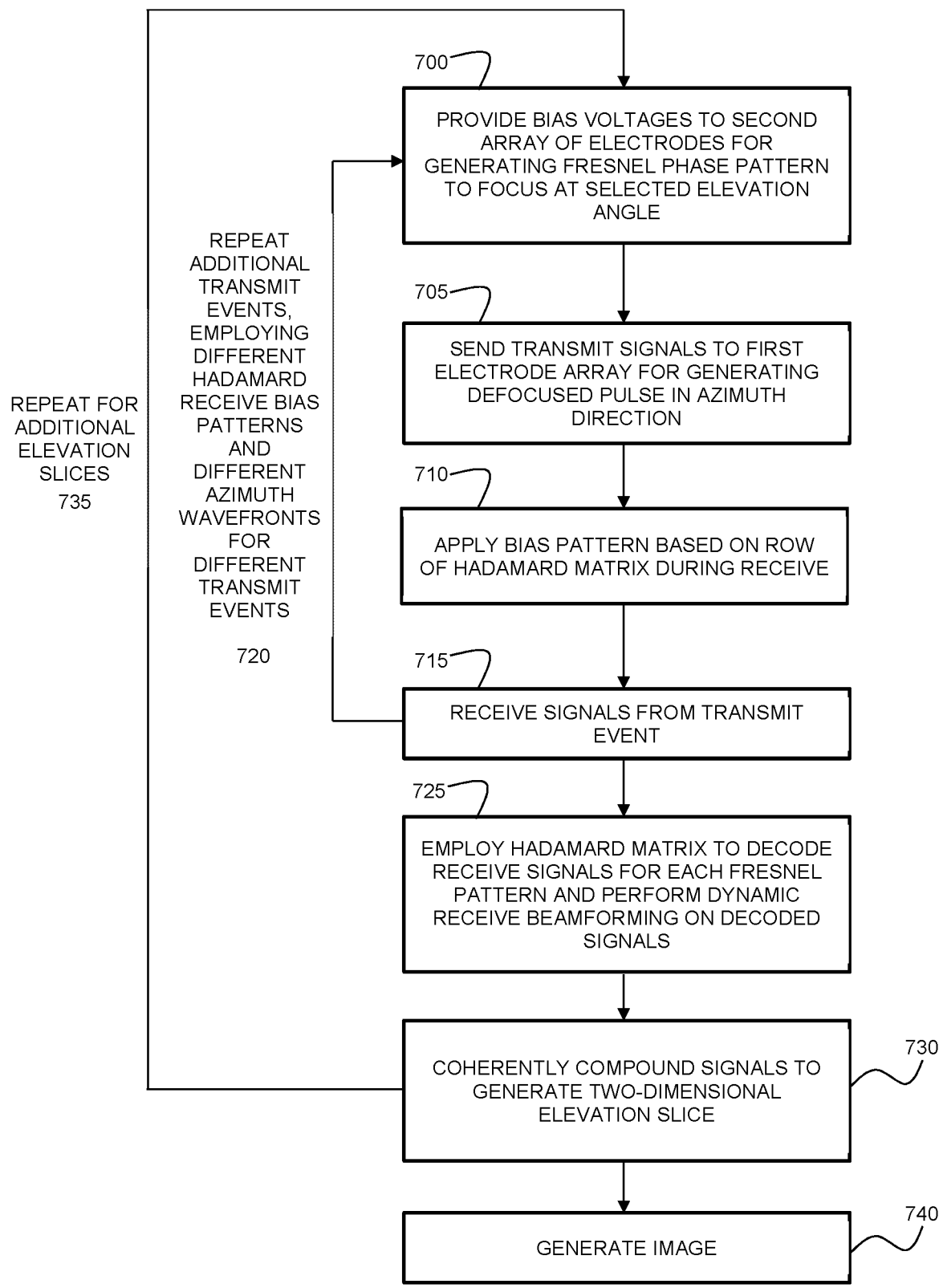
FIG. 23 is a flow chart illustrating an example method of performing three-dimensional imaging using a crossed-electrode array, in which Fresnel focusing is employed upon transmit in the elevation direction, and Hadamard encoding is employed upon receive, in parallel with coherent compounding in the azimuthal direction.

In another example of bias controlled three-dimensional imaging using a two-dimensional crossed-electrode array, the bias pattern across the bias electrodes can be used to focus ultrasound energy in the elevation direction by approximating a Fresnel lens, for example, as described in the preceding one-dimensional array example. According to the present example embodiment, a Fresnel lens bias pattern can be implemented in the elevation direction upon transmit, while Hadamard encoding of the bias patterns may be employed to build a synthetic receive aperture. These transmit/receive bias patterns create a two-way elevation focus that selects a slice of a 3D image volume. In the azimuth direction, the other electrode array may be employed for plane wave or diverging wave imaging. The Hadamard encoding approach requires N transmit/receive events to decode the contribution from each elevational element, where N is the number of electrodes that are biased for Hadamard encoding. In other words, N ultrasound pulses are transmitted per elevation Fresnel lens transmit bias pattern. During the N transmit/receive events the plane/diverging wave imaging in the azimuth direction is compounding simultaneously to improve the image quality of the slice. Using this approach, the number of transmit events required to build a 3D image depends on the number of elevational slices in the volume and the number of elevational elements of the crossed electrode array. In such as case, the frame rate would be: frame rate=PRF/[N*EL] where PRF is the pulse repetition frequency and EL is the number of elevation slices. FIG. 23 provides a flow chart illustrating an example implementation of this method, showing steps 700-740.

In one example implementation, the elevational slice selectivity can be further improved by changing the Fresnel lens pattern for each receive Hadamard coded pattern. The resulting compounding reduces the side lobe energy on the transmit focus. According to such an example embodiment, the transmit focused Fresnel pattern is changed for at least two Hadamard receive patterns (optionally all of the Hadamard receive patterns) by shifting the elevation focus spatially, as per the example embodiments described above. For example, at least two Fresnel patterns may correspond to different elevation focal depths and/or different elevation focal angles.

In many of the preceding example embodiments, a bias controlled Fresnel lens is employed to achieve a focus along a selected image line of a two-dimensional image region, or to achieve a focus in a selected elevation plane of a three-dimensional volume, selecting a single elevational image line or slice, respectively. Various embodiments have been described in which the Fresnel lens is employed on both transmit and receive, or on transmit only (e.g. with Hadamard encoding on receive). In addition, it has been shown that coherently compounding multiple Fresnel lens patterns on a single image line or slice decreases side lobe energy and increases image quality.

In some example embodiments, this concept can be extended to neighboring image lines or slices. For example, the signal data collected for the image lines or image slices near to a given image line or slice can be reused if the pulses for the neighbouring image lines or slices remain in phase or are phase adjusted at the focus. When the data from neighboring image lines or slices is reused in this way, the side lobe energy is suppressed further with no decrease in frame rate. For example, in some example implementations, the image lines or slices immediately adjacent to a given image line or image slice may be compounded, and this may be implemented for one or more image lines or image slices of the image data. In another example embodiment, two or more adjacent image lines or image slices on either or both sides of a given image line or image slice may be compounded. It will be understood that the compounding of signals from adjacent image lines or slices may be performed before or after Hadamard encoding and beamforming. Any of the preceding Fresnel-based imaging example embodiments, or variations thereof, may be adapted according to the present example embodiment involving the compounding of image data from adjacent image lines or image slices.

Figure 17:
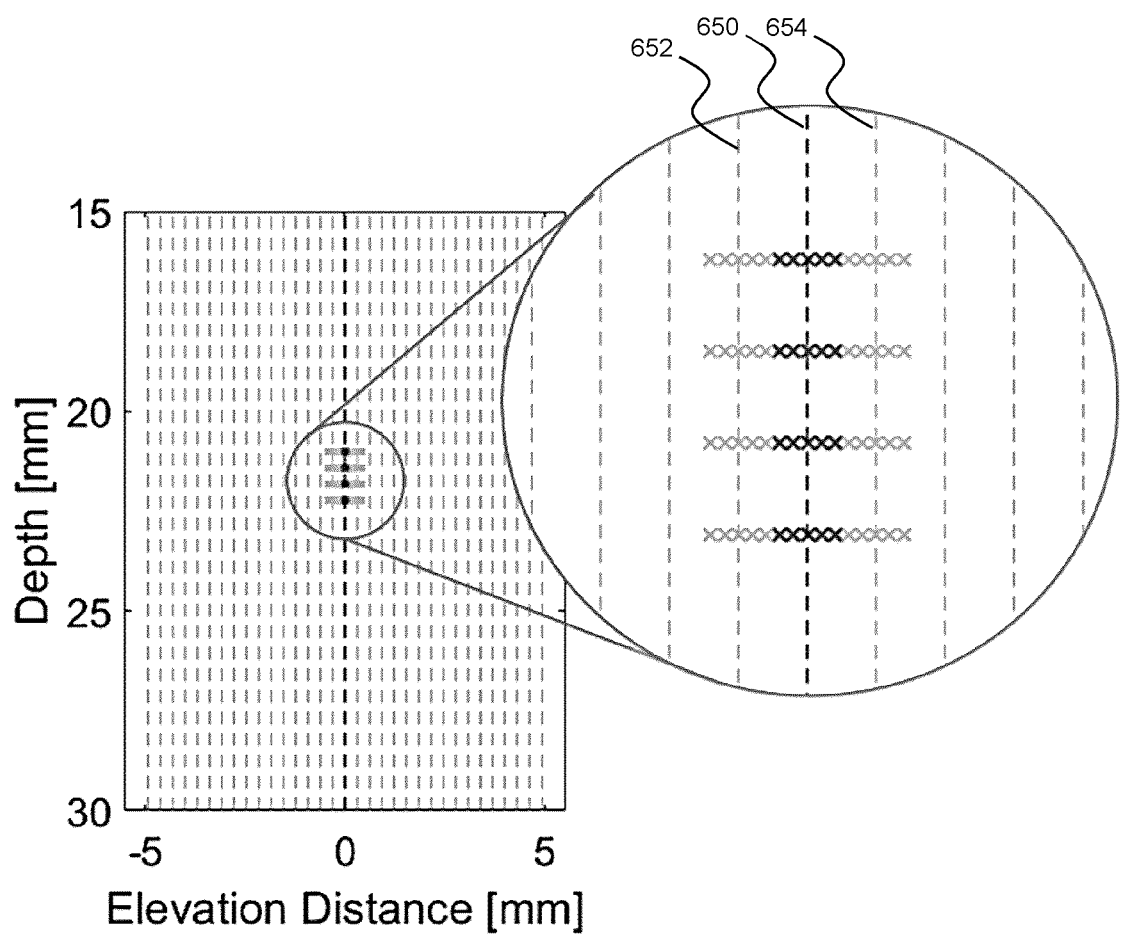
FIG. 17 illustrates an example implementation in which 20 Fresnel focal locations are used per line and the two neighboring imaging lines are reused for the current line.
Figure 18A:
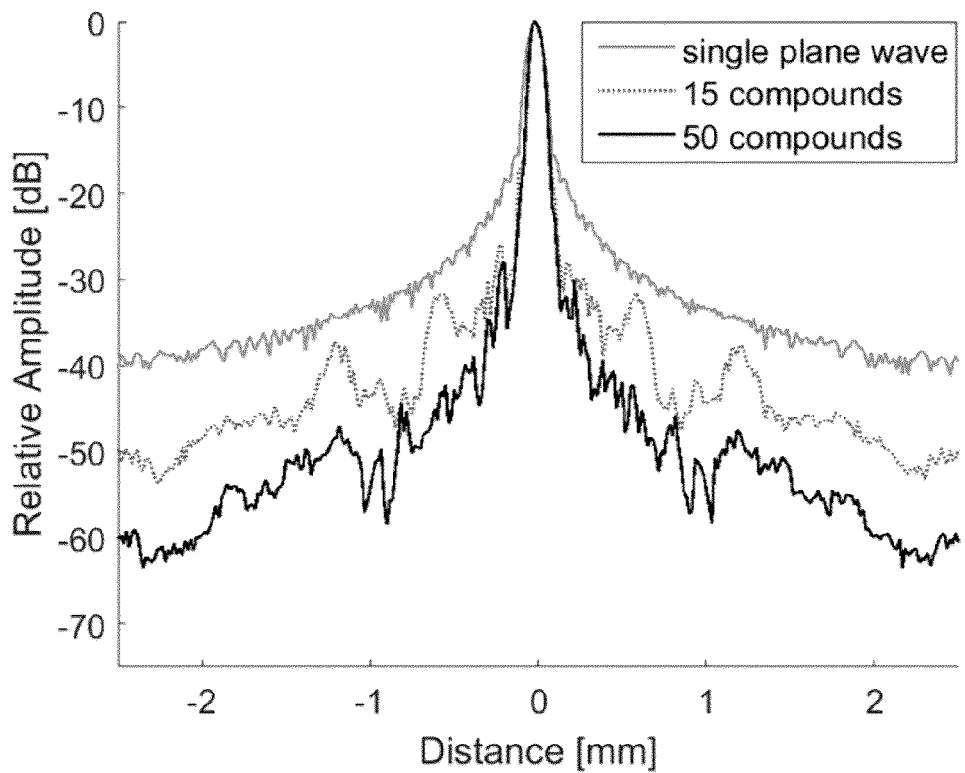
FIGS. 18A and 18B plot two-way radiation patterns for (A) on axis and (B) off axis cases showing improvement made by compounding 15 and 50 Fresnel wave images compared to a single plane wave image.
Figure 18B:
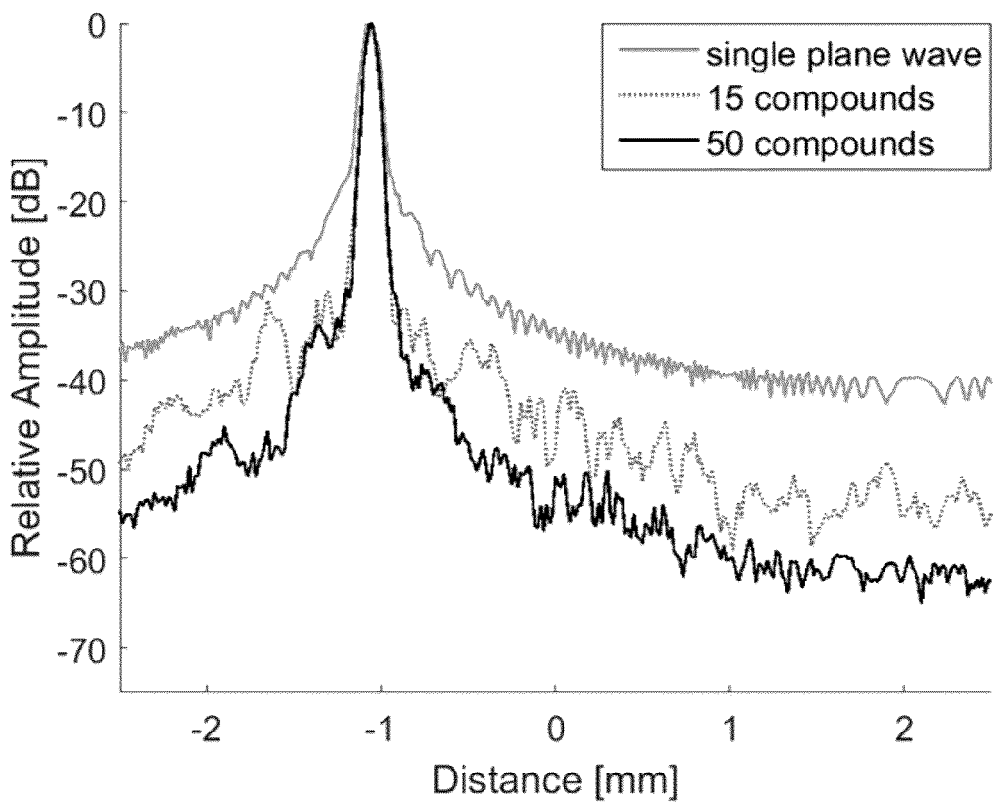

An example implementation of such an embodiment is illustrated in FIG. 17, in which 20 Fresnel focal locations are used per line and the two neighboring image lines (652 and 654) are reused for the current image line 650. Examples of such side lobe energy reduction for multi-line or multi-slice compounding are provided in Example 4 below.

EXAMPLES

The following examples are presented to enable those skilled in the art to understand and to practice embodiments of the present disclosure. They should not be considered as a limitation on the scope of the disclosure, but merely as being illustrative and representative thereof.

Figure 9A:
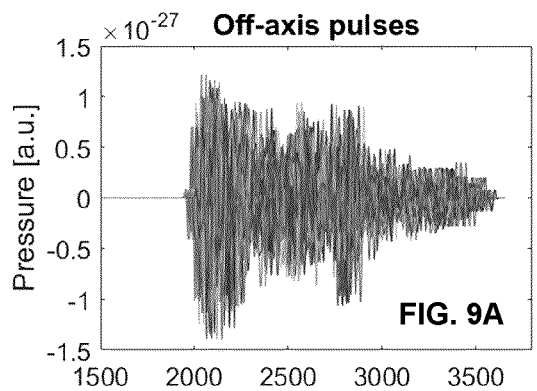
FIGS. 9A-F plot simulated RF pulse data for Fresnel focusing using 36 Fresnel phase patterns for an axially-focused configuration, collected at an off-axis angle of 30 degrees (FIGS. 9A-B) and on-axis (FIGS. 9C-F).
Figure 9B:
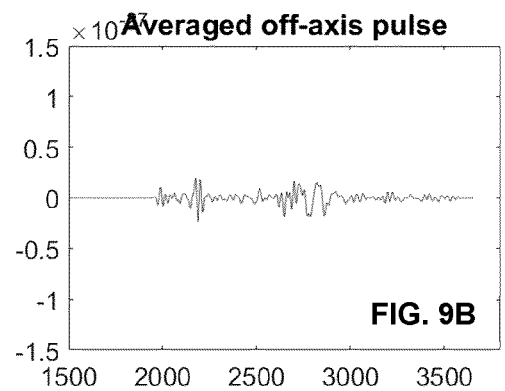
Figure 9C:
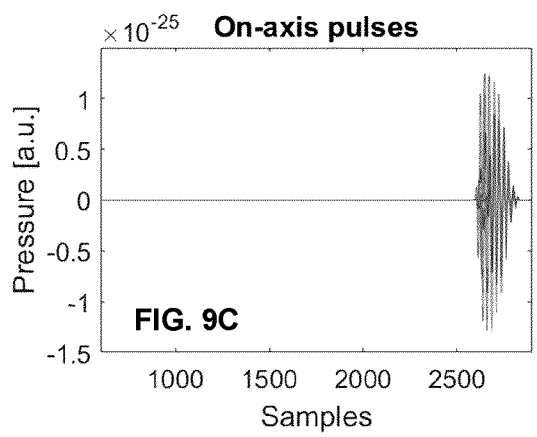
Figure 9D:
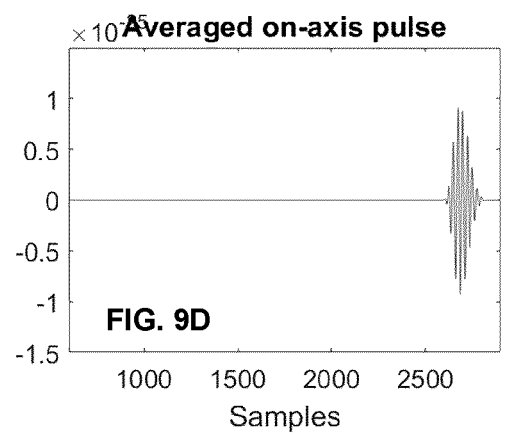
Figure 9E:
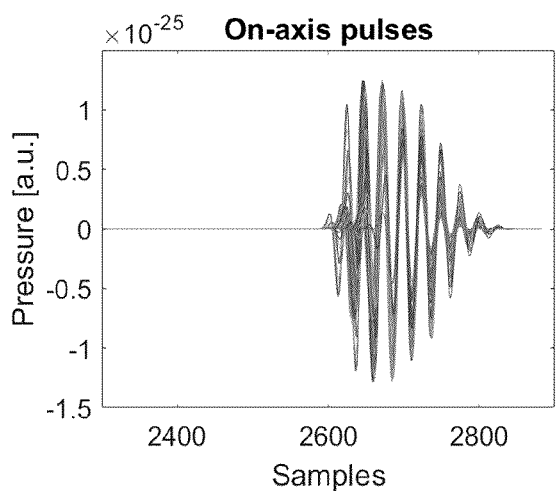
Figure 9F:
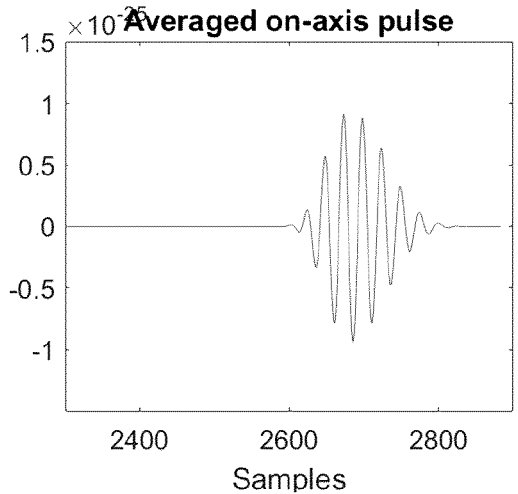

Example 1: Simulation of Fresnel Coherent Compounded Focusing Using Fresnel Phase Patterns Corresponding to Spatially Different Focal Locations In the present example, a 40 MHz 1D phased array was simulated using Field II, and coherently compounded Fresnel focusing was performed by selecting Fresnel phase patterns corresponding to different locations near a common focal point. Three example Fresnel patterns generated by moving the focal point down the central axis away from the array are shown in FIGS. 2A-C. Two-way pulse echo measurements were collected for the field of interest and compounded for each Fresnel pattern (n=36). FIGS. 9A-F show simulated RF data from 30 degrees off-axis (FIGS. 9A-B) compared to the on-axis case (FIGS. 9C-F). FIGS. 9A, 9C and 9E show the 36 separate pulse echoes, while FIGS. 9B, 9D and 9F show the averaged pulses. As can be seen from FIGS. 9A-B, the off-axis energy compounds incoherently and the average is significantly reduced. In contrast, the on-axis pulses (FIGS. 9C-F) have the same phase and the average signal does not lose strength.

As can be seen in FIGS. 9C-F, there is variability in the amplitude of the focused pulse for each Fresnel pattern, which explains why the compounded pulse is smaller in amplitude than the largest single pulse.

Figure 10:
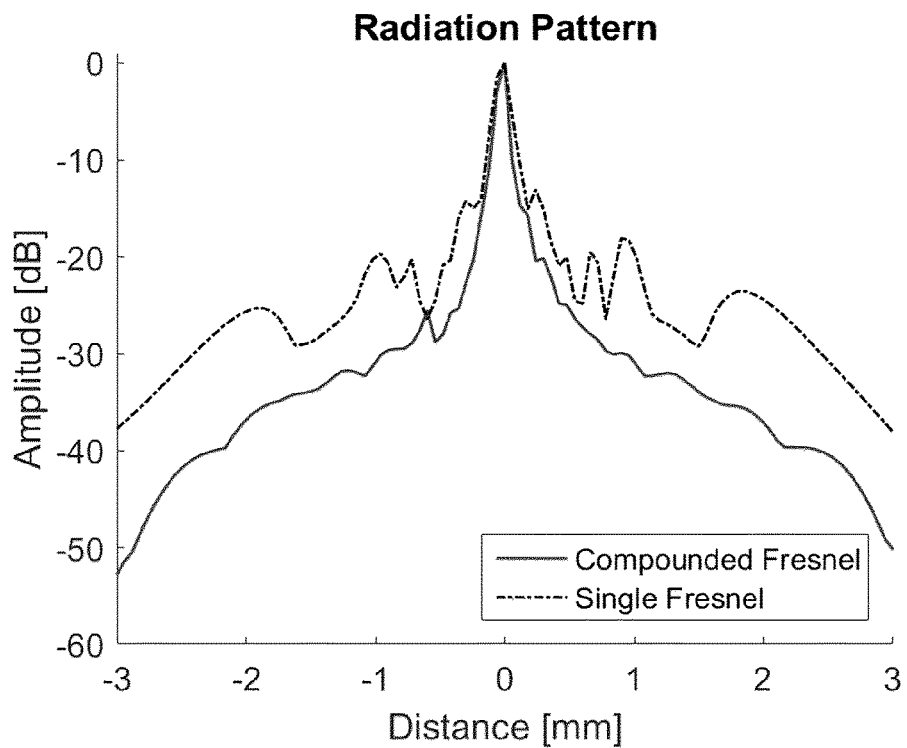
FIG. 10 plots the simulated two-way radiation pattern for signals received based on a single Fresnel pattern, and based on a coherently compounded set of receive signals respectively associated a plurality of different Fresnel phase patterns generated using different focal regions for each pattern.

In the present example, a 13 dB improvement in main lobe to secondary lobe energy was achieved by compounding. This is close to the theoretical $\sqrt{n}$ improvement of 15.5 dB. The improvement to the two-way radiation pattern is shown in FIG. 10. The secondary lobe levels are reduced while maintaining main lobe width. This example was performed using 36 compounded events to illustrate the concept, however, the results will improve with the number of averages. In addition, the unique Fresnel patterns could be generated by moving the focal spot laterally as well as axially or by changing the offset phases used to quantize to 0 or $\lambda/2$ (as shown in the example below).

Figures 11A, 11B:
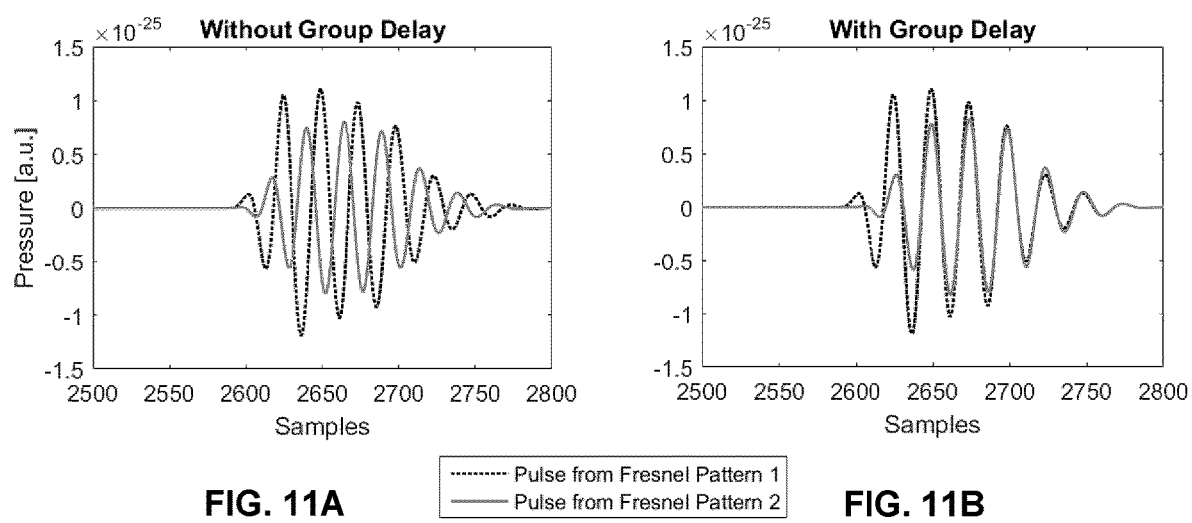
FIGS. 11A-B plot the simulated pressure generated in the focal region based on two different Fresnel phase patterns, showing results generated with (FIG. 11B) and without (FIG. 11A) group delay compensation for the difference in time of flight for pulses emitted using the two different Fresnel phase patterns.

Group delay corrections were applied to the transmit and receive pulses in order to correct for time-of-flight variations among the different Fresnel phase patterns. FIGS. 11A-B illustrate the effect of group delay compensation, showing two example pulses at the focal point from two different Fresnel phase patterns. When the group delay is not used the pulses at the focus are out of phase, as shown in FIG. 11A. However, when the group delay is added the pulses are in phase and constructively interfere, as shown in FIG. 11B.

Figure 12A:
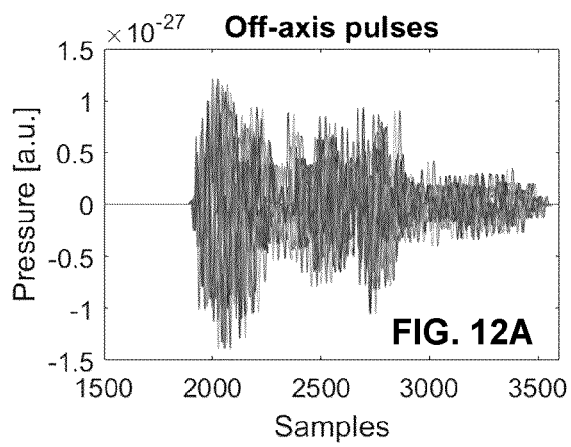
FIGS. 12A-F plot simulated RF pulse data for Fresnel focusing using 16 Fresnel phase patterns for an axially-focused configuration, collected at an off-axis angle of 30 degrees (FIGS. 12A-B) and on-axis (FIGS. 12C-F).
Figure 12B:
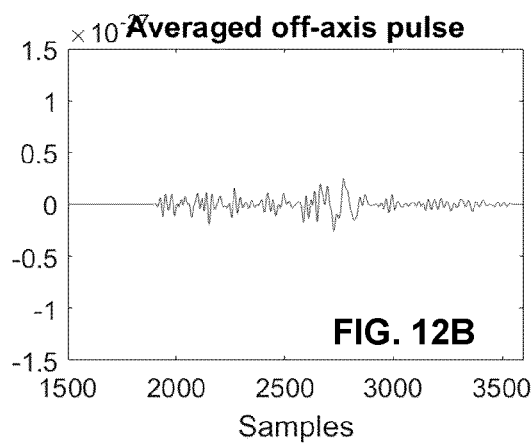
Figure 12C:
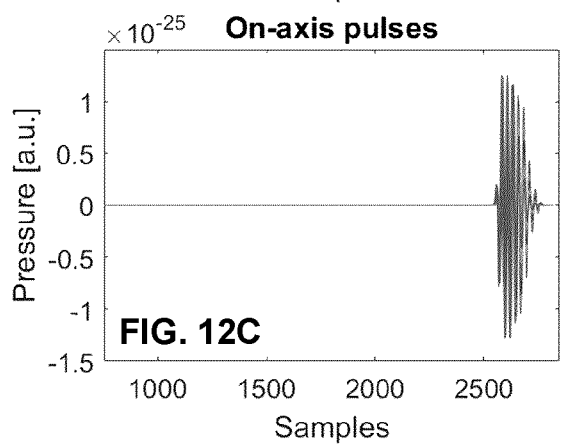
Figure 12D:
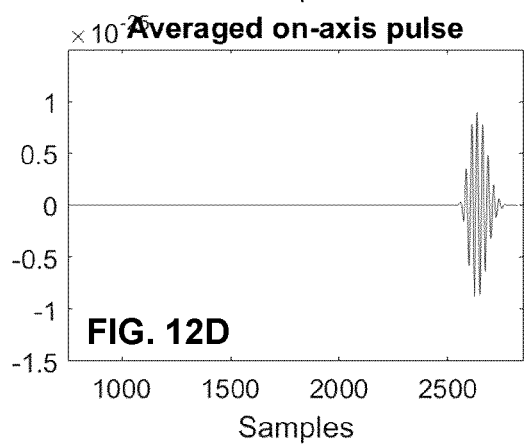
Figure 12E:
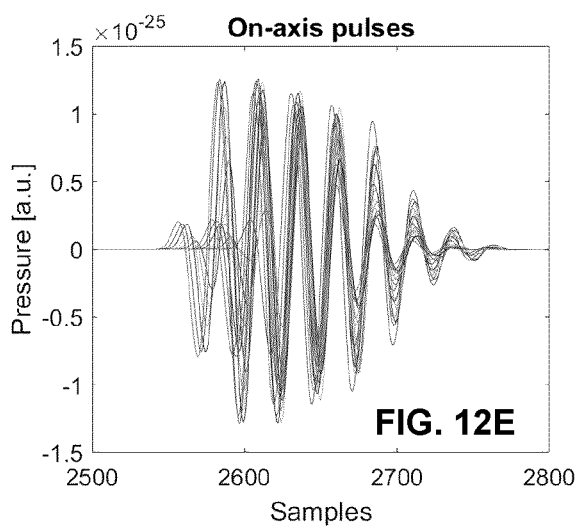
Figure 12F:
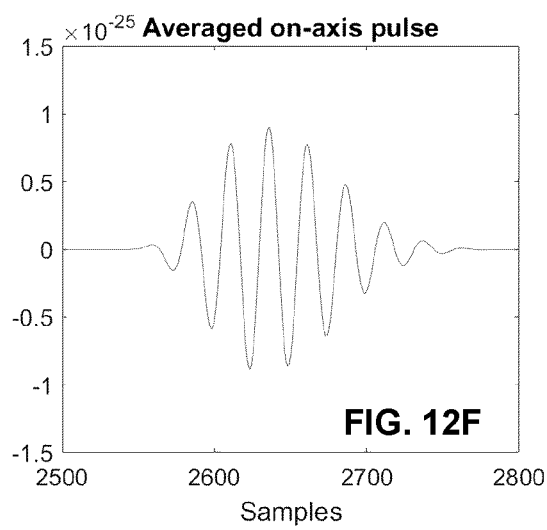
Figure 13:
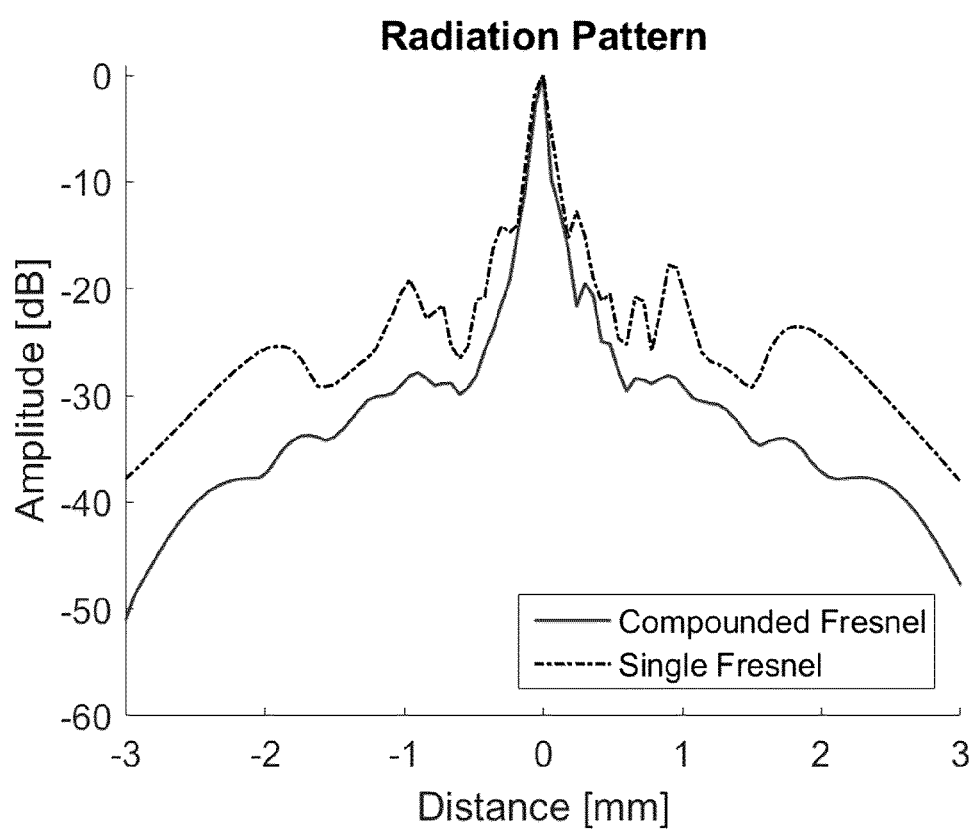
FIG. 13 plots the simulated two-way radiation pattern for signals received based on a single Fresnel pattern, and based on a coherently compounded set of receive signals respectively associated with a plurality of different Fresnel phase patterns generated using a different phase offset for each pattern.

Example 2: Simulation of Fresnel Coherent Compounded Focusing Using Fresnel Phase Patterns Corresponding to Phase Offsets The present example described simulations that were performed to illustrate the performance improvement with compounding when different Fresnel patterns are generated using a variation in the phase offset prior to quantization. The 40 MHz 1D phased array described in the previous example was simulated, and two-way pulse echo measurements were collected for the field of interest and compounded for each Fresnel pattern. In this present example, 16 unique Fresnel patterns were generated by changing the phase offset value between 0 rad and $2\pi$ rad (n=16). FIGS. 12A-F show simulated RF data from 30 degrees off-axis (FIGS. 12A-B) compared to the on-axis case (FIGS. 12C-F). FIGS. 12A, 12C and 12E show the 16 separate pulse echoes, while FIGS. 12B, 12D and 12F show the averaged pulses. As can be seen in FIGS. 12A-B, the off-axis energy compounds incoherently and the average is significantly reduced. In contrast, the pulses on-axis have overlapping phase, as can be seen in FIGS. 12E-F. In this example, a 12.2 dB improvement in main lobe to secondary lobe energy was achieved by compounding. The improvement to the two-way radiation pattern is shown in FIG. 13. Group delay corrections were applied to the transmit and receive pulses in order to correct for time-of-flight variations due to the different phase offsets employed when generating the different Fresnel phase patterns.

Example 3: Simulation of Bias Controlled Fresnel Wavefront Imaging for 1D Array

In order to illustrate the bias controlled Fresnel wavefront imaging with dynamic receive beamforming was completed by modelling a 40 MHz 64 element 1D array using Field II

[3]. The results are illustrated in FIGS. 16A and 16B, showing a radiation pattern profile of a scatterer on axis and a scatterer at the edge of the array. Increasing the number of Fresnel wave compounds reduces the side lobe levels significantly which translates to increased image quality.

Figure 19A:
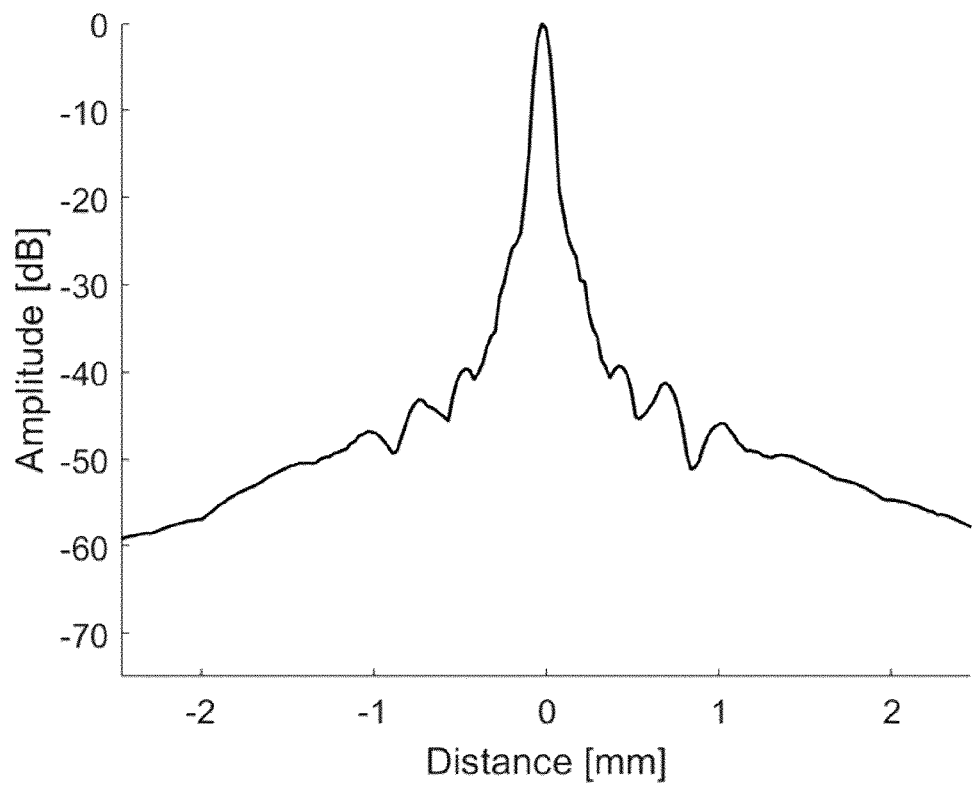
FIGS. 19A and 19B plot two-way radiation patterns for (A) on axis and (B) off axis cases implementing a Fresnel lens on transmit and a Hadamard decoded synthetic receive aperture.
Figure 19B:
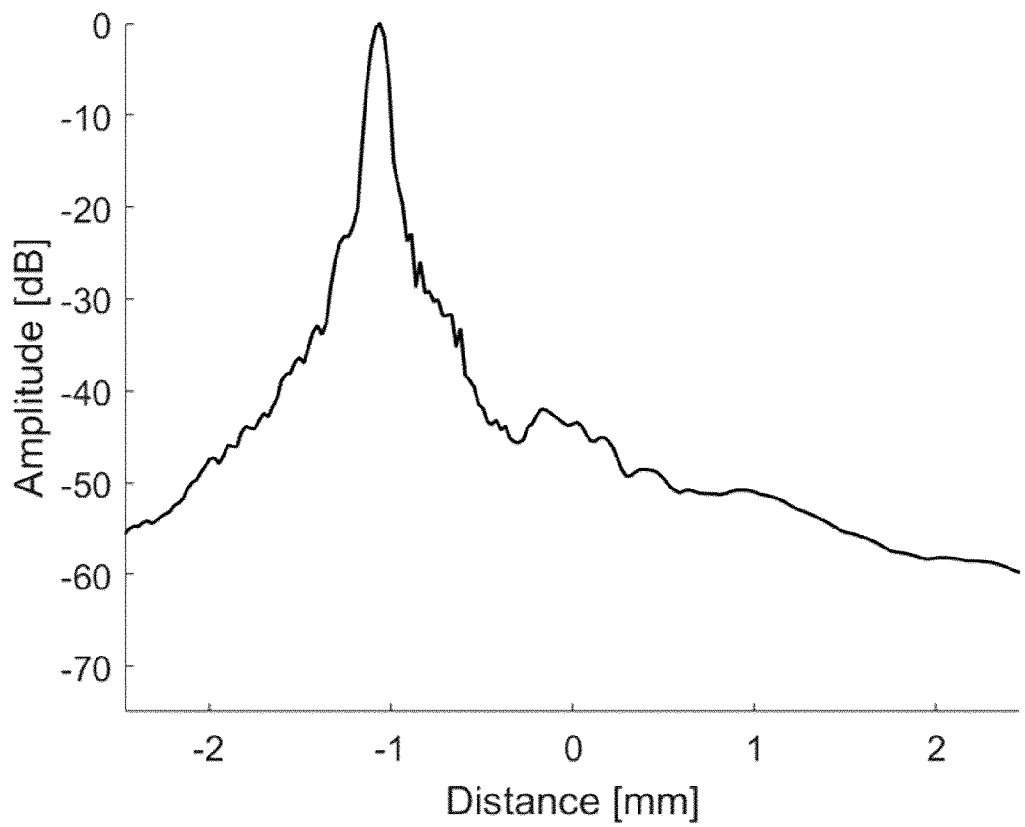

Simulations of a bias controlled Fresnel lens with Hadamard encoded receive bias patterns were also completed by modelling a 40 MHz 64 element 1D array using Field II. The results are illustrated in FIGS. 19A and 19B, which show a radiation pattern profile on axis and at the edge of the array. The simulations were completed with 64 transmit/receive events to decode the received contribution from each element using the Hadamard matrix. The decoded received signals are beamformed, however, the focus on transmit is provided by the Fresnel lens bias pattern.

Example 4: Compounding of Data from Neighbouring Image Lines (or Elevation Slices)

Figure 20A:
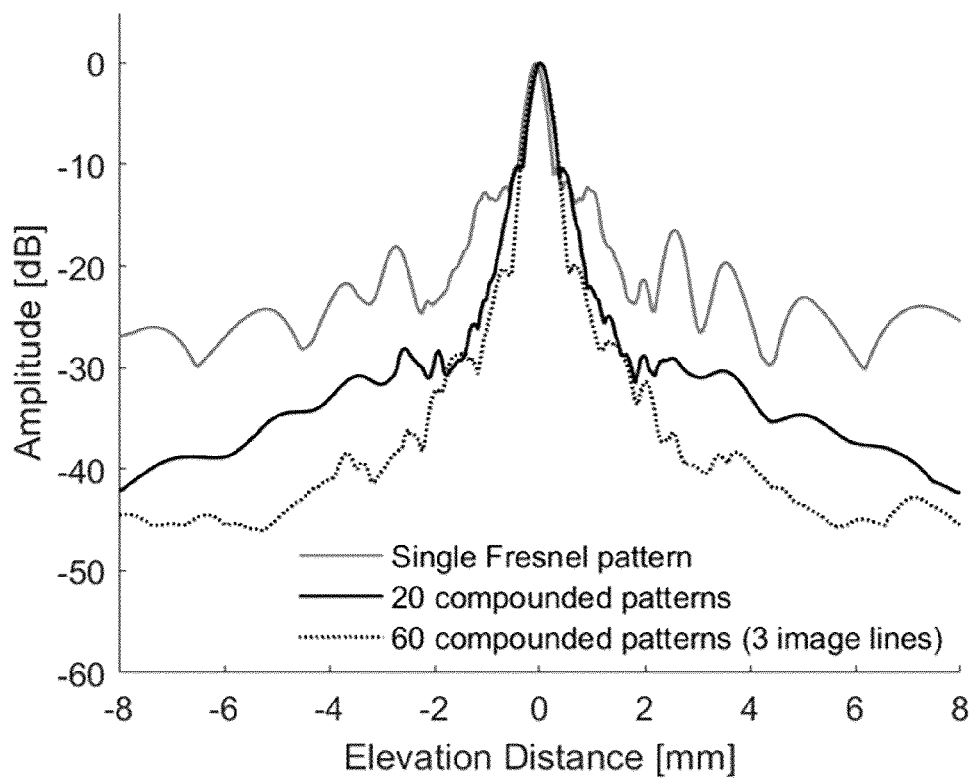
FIGS. 20A and 20B plot two-way radiation patterns for (A) on axis and (B) off axis cases implementing neighboring line compounding on 3 image lines.
Figure 20B:
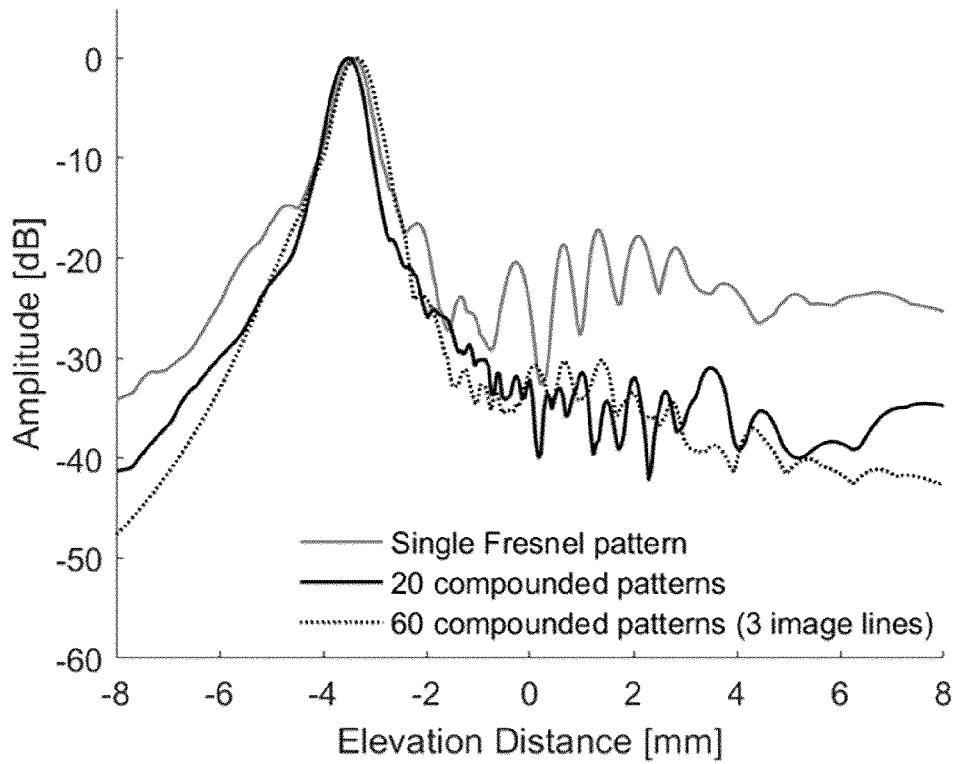

Simulations of a bias controlled Fresnel lens on transmit and receive while compounding data from neighboring elevational lines were completed by modelling a 10 MHz 64 element 1D array using Field II. The imaging lines and Fresnel lens focal locations are shown in FIG. 17. In this example, 20 compounds are used for each imaging line and the data from the two neighboring image lines are reused for the current line for a total of 60 compounds, where the compounding was performed after Hadamard decoding. The results are illustrated in FIGS. 20A and 20B, showing a radiation pattern profile on axis and at the edge of the array and comparing 20 compounds on a single line to 60 compounds on three imaging lines.

Figure 21A:
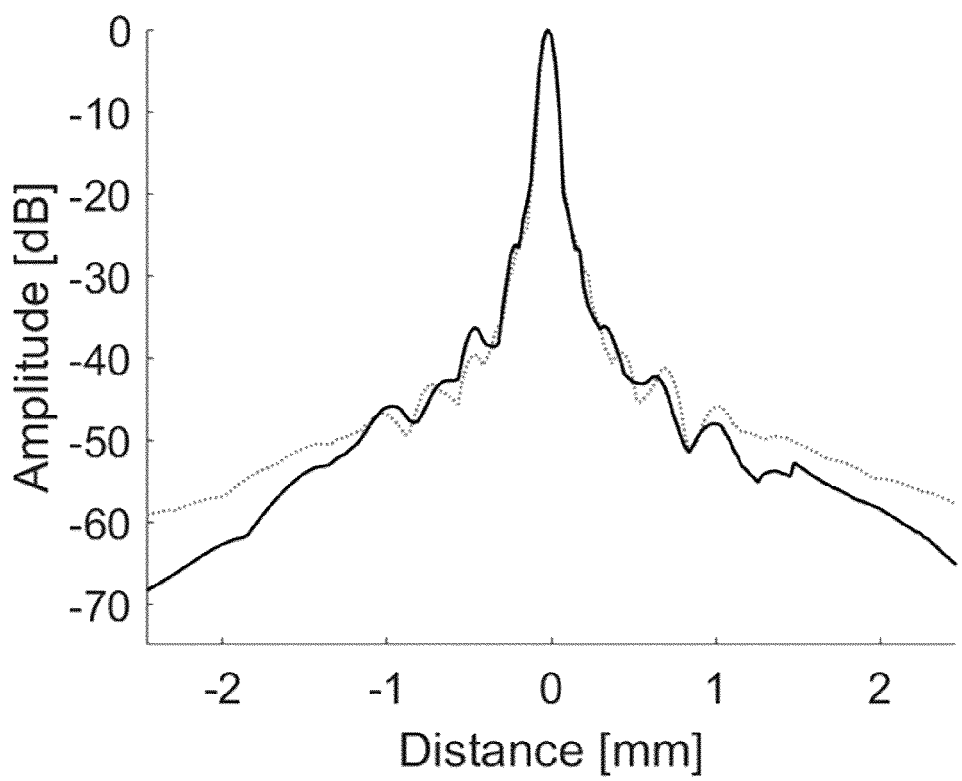
FIGS. 21A and 21B plot two-way radiation patterns for (A) on axis and (B) off axis cases implementing a Fresnel lens on transmit and a Hadamard decoded synthetic receive aperture and reusing the data from neighboring image lines (three lines total) to compound. The radiation pattern from a single line is shown as a dotted line for reference.
Figure 21B:
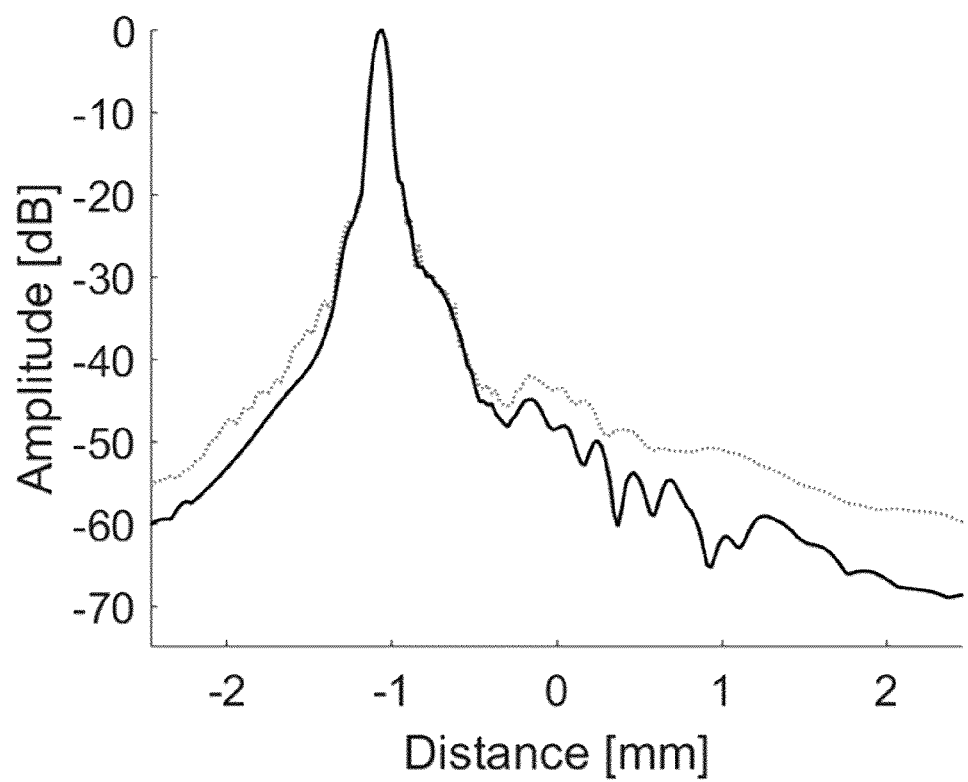

In a second example of compounding data from neighboring elevational slices, a 40 MHz 64 element 2D crossed-electrode array was simulated using Field II. A bias controlled Fresnel lens was implemented on transmit and Hadamard encoded patterns were applied on receive. Data from image lines on either side of the current slice was collected and coherently compounded prior to Hadamard decoding and beamforming. The resulting radiation patterns in the elevation direction are shown in FIGS. 21A and 21B for a focus on axis as well as near the edge of the array.

FIGS. 22A-22D show plots that demonstrate the effect of compounding neighbouring elevation slices on pulse length for a two-dimensional crossed electrode array, showing (A) the processed pulse for a single Fresnel lens on transmit and Hadamard receive encoding in elevation, with a focus on center, (B) the processed pulse for a single Fresnel lens on transmit and Hadamard receive encoding in elevation, with a focus to a wide angle, (C) the processed pulse for a single Fresnel lens on transmit and Hadamard receive encoding in elevation and compounding of three neighbouring elevation slices, with a focus on center, and (D) the processed pulse for a single Fresnel lens on transmit and Hadamard receive encoding and compounding of three neighbouring elevation slices, with a focus to a wide angle. The vertical axis is arbitrary pulse amplitude, and the horizontal axis is time.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Thereof what is claimed is:

1. An ultrasound imaging system comprising:
an ultrasound array comprising a plurality of ultrasound array elements defined between a first electrode array and a second electrode array;
wherein electrodes of said first electrode array are spaced along, and extend perpendicular to, an azimuth direction, and electrodes of said second electrode array are spaced along, and extend perpendicular to, an elevation direction, such that said first electrode array and said second electrode array are provided in a crossed electrode configuration; and
wherein each ultrasound array element is capable of acoustic transduction such that a phase of ultrasound waves emitted therefrom is dependent on a polarity of a bias voltage applied thereto;
the ultrasound imaging system further comprising control and processing circuitry operably connected to said first electrode array and said second electrode array, said control and processing circuitry comprising a processor and a memory, wherein said processor is configured to execute instructions stored in said memory for performing the steps of:
a) controlling said ultrasound array to sequentially transmit a plurality of ultrasound pulses such that, for each ultrasound pulse of the plurality of ultrasound pulses, a set of transmit signals are sent to respective electrodes of said first electrode array while providing a set of bias voltages to respective electrodes of said second electrode array;
wherein the transmit signals are provided to said first electrode array such that each ultrasound pulse is unfocused in the azimuth direction, and such that the plurality of ultrasound pulses have respective wavefronts suitable for performing coherent compound imaging in the azimuth direction; and
wherein the bias voltages are provided to said second electrode array to form a set of Fresnel phase patterns, wherein each Fresnel phase pattern is configured to focus a respective ultrasound pulse at, or proximal to, a selected elevation slice focus characterized by a selected elevation angle, and wherein at least a subset of the Fresnel phase patterns are different Fresnel phase patterns;
b) coherently compounding receive signals responsively received by said first electrode array after transmitting each ultrasound pulse, thereby obtaining a two-dimensional image data set corresponding to the selected elevation angle, and wherein Fresnel secondary lobes associated with each Fresnel phase pattern are reduced via coherent compounding of the receive signals associated with the different Fresnel phase patterns;
c) repeating steps a) and b) one or more times to collect additional two-dimensional data sets associated with one or more additional elevation angles, thereby obtaining a three-dimensional image data set comprising a plurality of two-dimensional image data sets; and
d) processing the three-dimensional image data to generate one or more images.

2. The ultrasound imaging system according to claim 1 wherein said control and processing circuitry is configured such that each of said set of Fresnel phase patterns are different.

3. The ultrasound imaging system according to claim 2 wherein said different Fresnel phase patterns are selected such that a reduction factor in elevation secondary lobe energy, relative to an elevation secondary lobe energy that would be obtained using common Fresnel phase patterns for all of the plurality of ultrasound pulses, is within 25% of the square root of the number of ultrasound pulses in the plurality of ultrasound pulses.

4. The ultrasound imaging system according to claim 1 wherein said control and processing circuitry is configured such that at least two different Fresnel phase patterns are generated by selecting, for each of the at least two different Fresnel phase patterns, a different phase offset prior to phase wrapping.

5. The ultrasound imaging system according to claim 4 wherein said control and processing circuitry is configured such that for each Fresnel phase pattern generated using a phase offset, a group delay is added to transmit signals respectively associated therewith to compensate for the phase offset.

6. The ultrasound imaging system according to claim 1 wherein said control and processing circuitry is configured such that at least two different Fresnel phase patterns are generated by selecting, for each of the at least two different Fresnel phase patterns, a different elevation focal depth.

7. The ultrasound imaging system according to claim 6 wherein said control and processing circuitry is configured such that for each Fresnel phase pattern associated with a different elevation focal depth, a group delay is added to transmit signals respectively associated therewith to compensate for the different elevation focal depth.

8. The ultrasound imaging system according to claim 1 wherein said control and processing circuitry is configured such that at least two different Fresnel phase patterns are generated by selecting, for each of the at least two different Fresnel phase patterns, a different elevation angle.

9. The ultrasound imaging system according to claim 1 wherein said control and processing circuitry is configured to generate the transmit signals such that the wavefronts of each ultrasound pulse, within the azimuth plane, are linear, and such that the wavefronts associated with different pulses are angled in different directions in the azimuth plane.

10. The ultrasound imaging system according to claim 1 wherein said control and processing circuitry is configured to generate the transmit signals such that each ultrasound pulse propagates with wavefronts that are diverging in the azimuth plane.

11. The ultrasound imaging system according to claim 10 wherein said control and processing circuitry is configured to generate the transmit signals such that the wavefronts respectively associated with of each ultrasound pulse have different virtual source locations.

12. The ultrasound imaging system according to claim 1 wherein said control and processing circuitry is configured to provide bias signals to said second electrode array when detecting the receive signals, such that Fresnel phase patterns are also formed for performing elevation focusing.

13. The ultrasound imaging system according to claim 12 wherein said control and processing circuitry is configured such that the same Fresnel phase patterns are formed during transmit and receive.

14. The ultrasound imaging system according to claim 12 wherein said control and processing circuitry is configured such that different Fresnel phase patterns are formed during transmit and receive.

15. The ultrasound imaging system according to claim 1 wherein said control and processing circuitry is configured such that elevation focusing of one or more ultrasound pulses is performed by employing a plurality of split and delay elevation sub-apertures in combination with Fresnel phase focusing.

16. The ultrasound imaging system according to claim 1 wherein said ultrasound array elements are defined, within an electrostrictive layer, by said first electrode array and by said second electrode array.

17. The ultrasound imaging system according to claim 1 any ono of claims 1 to 15 wherein said ultrasound array elements comprise capacitive micromachined ultrasound transducer (CMUT) array elements.

18. The ultrasound imaging system according to claim 1 wherein said ultrasound array elements are kerfed in at least one dimension.

19. The ultrasound imaging system according to claim 1 wherein said ultrasound array elements are partially kerfed in at least one dimension.

20. An ultrasound imaging system comprising:
an ultrasound array comprising a plurality of ultrasound array elements defined between a first electrode array and a second electrode array;
wherein electrodes of said first electrode array are spaced along, and extend perpendicular to, an azimuth direction, and electrodes of said second electrode array are spaced along, and extend perpendicular to, an elevation direction, such that said first electrode array and said second electrode array are provided in a crossed electrode configuration; and
wherein each ultrasound array element is capable of acoustic transduction such that a phase of ultrasound waves emitted therefrom is dependent on a polarity of a bias voltage applied thereto;
the ultrasound imaging system further comprising control and processing circuitry operably connected to said first electrode array and said second electrode array, said control and processing circuitry comprising a processor and a memory, wherein said processor is configured to execute instructions stored in said memory for performing the steps of:
a) controlling said ultrasound array to sequentially transmit a plurality of ultrasound pulses such that, for each ultrasound pulse of the plurality of ultrasound pulses, a set of transmit signals are sent to respective electrodes of said first electrode array while providing a set of transmit bias voltages to respective electrodes of said second electrode array;
wherein the transmit signals are provided to said first electrode array such that each ultrasound pulse is unfocused in the azimuth direction, and such that the plurality of ultrasound pulses have respective wavefronts suitable for performing coherent compound imaging in the azimuth direction; and
wherein the transmit bias voltages are provided to said second electrode array to form a Fresnel phase pattern configured to focus a respective ultrasound pulse at a selected elevation slice focus characterized by a selected elevation angle; and
applying receive bias voltages to said second electrode array such that each ultrasound pulse has associated therewith a unique set of receive bias voltages, and wherein the unique sets of receive bias voltages respectively associated with the ultrasound pulses correspond to different rows of a Hadamard matrix;
b) compounding receive signals received by said first electrode array during application of the receive bias voltages for each ultrasound pulse, wherein compounding is performed by:
employing the Hadamard matrix to decode the receive signals, and employing dynamic receive beamforming of the decoded receive signals in the elevation direction to generate a two-way focus associated with the selected elevation angle; and coherently compounding the decoded and beamformed receive signals to obtain two-dimensional image data set corresponding to the selected elevation angle;

c) repeating steps a) and b) one or more times to collect additional two-dimensional data sets associated with one or more additional elevation angles, thereby obtaining a three-dimensional image data set comprising a plurality of two-dimensional image data sets; and d) processing the three-dimensional image data to generate one or more images.

21. The system according to claim 20, wherein said control and processing circuitry is further configured to reduce side lobe energy associated by at least one elevation slice by coherently compounding receive signals associated with one or more adjacent elevation slices prior to Hadamard decoding and beamforming.

22. The system according to claim 20 wherein at least two of the Fresnel phase patterns employed for a given elevation slice are different, thereby reducing side lobe energy.

23. The system according to claim 20 at least two of the Fresnel phase patterns employed for a given elevation slice have a relative shift in elevation angle or elevation focal depth.

24. An ultrasound imaging system comprising:

an ultrasound array comprising a plurality of ultrasound array elements defined between a first electrode array and a second electrode array;

wherein electrodes of said first electrode array are spaced along, and extend perpendicular to, an azimuth direction, and electrodes of said second electrode array are spaced along, and extend perpendicular to, an elevation direction, such that said first electrode array and said second electrode array are provided in a crossed electrode configuration; and wherein each ultrasound array element is capable of acoustic transduction such that a phase of ultrasound waves emitted therefrom is dependent on a polarity of a bias voltage applied thereto;

the ultrasound imaging system further comprising control and processing circuitry operably connected to said first electrode array and said second electrode array, said control and processing circuitry comprising a processor and a memory, wherein said processor is configured to execute instructions stored in said memory for performing the steps of:

a) controlling said ultrasound array to sequentially transmit a plurality of ultrasound pulses such that, for each ultrasound pulse of the plurality of ultrasound pulses, a set of transmit signals are sent to respective electrodes of said first electrode array while providing a set of transmit bias voltages to respective electrodes of said second electrode array;

wherein the transmit signals are provided to said first electrode array such that each ultrasound pulse is unfocused in the azimuth direction, and such that the plurality of ultrasound pulses have respective wavefronts suitable for performing coherent compound imaging in the azimuth direction; and wherein the transmit bias voltages are provided to said second electrode array to form a set of Fresnel phase patterns, wherein each Fresnel phase pattern is configured to form a respective defocused Fresnel wave, and wherein at least a subset of the Fresnel phase patterns are different Fresnel phase patterns, and wherein each Fresnel phase pattern is repeated for a plurality of ultrasound pulses;

applying receive bias voltages to said second electrode array such that each ultrasound pulse corresponding to a given Fresnel phase pattern has associated therewith a unique set of receive bias voltages, and wherein the unique sets of receive bias voltages respectively correspond to different rows of a Hadamard matrix;

b) compounding receive signals received by said first electrode array during application of the receive bias voltages for each ultrasound pulse, wherein compounding is performed by:

employing the Hadamard matrix to decode the receive signals for each Fresnel pattern; and coherently compounding the decoded receive signals in the elevation and azimuthal direction to obtain three dimensional image data; and c) processing the three-dimensional image data to generate one or more images.

* * * * *

UNITED STATES PATENT AND TRADEMARK OFFICE
CERTIFICATE OF CORRECTION

PATENT NO. : 11,255,965 B2
APPLICATION NO. : 16/469903
DATED : February 22, 2022
INVENTOR(S) : Jeremy Brown et al.

It is certified that error appears in the above-identified patent and that said Letters Patent is hereby corrected as shown below:

In the Claims

Column 36, Lines 5 through 8, should read as follows:
17. The ultrasound imaging system according to claim 1 wherein said ultrasound array elements comprise capacitive micromachined ultrasound transducer (CMUT) array elements.

Signed and Sealed this
Seventeenth Day of January, 2023

Katherine Kelly Vidal
*Director of the United States Patent and Trademark Office*